(12) United States Patent
Yoshida et al.

(10) Patent No.: US 9,403,883 B2
(45) Date of Patent: Aug. 2, 2016

(54) PROTEIN HAVING AFFINITY FOR IMMUNOGLOBULIN, AND IMMUNOGLOBULIN-BINDING AFFINITY LIGAND

(75) Inventors: Shinichi Yoshida, Hyogo (JP); Dai Murata, Hyogo (JP); Masayuki Takano, Hyogo (JP); Junya Akagi, Hyogo (JP); Keita Iguchi, Hyogo (JP); Yoshiyuki Nakano, Hyogo (JP)

(73) Assignee: KANEKA CORPORATION, Osaka-shi, Osaka (JP)

( * ) Notice: Subject to any disclaimer, the term of this patent is extended or adjusted under 35 U.S.C. 154(b) by 0 days.

(21) Appl. No.: 13/258,655

(22) PCT Filed: Mar. 24, 2010

(86) PCT No.: PCT/JP2010/055030
§ 371 (c)(1),
(2), (4) Date: Dec. 13, 2011

(87) PCT Pub. No.: WO2010/110288
PCT Pub. Date: Sep. 30, 2010

(65) Prior Publication Data
US 2012/0208234 A1     Aug. 16, 2012

(30) Foreign Application Priority Data
Mar. 24, 2009    (JP) ................................. 2009-071766

(51) Int. Cl.
| | | |
|---|---|---|
| C07K 14/31 | (2006.01) |
| C07K 14/47 | (2006.01) |
| B01J 20/286 | (2006.01) |
| B01J 20/32 | (2006.01) |
| B01D 15/38 | (2006.01) |

(52) U.S. Cl.
CPC ............... *C07K 14/47* (2013.01); *B01J 20/286* (2013.01); *B01J 20/3244* (2013.01); *B01J 20/3274* (2013.01); *C07K 14/31* (2013.01); *B01D 15/3809* (2013.01)

(58) Field of Classification Search
None
See application file for complete search history.

(56) References Cited

U.S. PATENT DOCUMENTS

| | | | |
|---|---|---|---|
| 5,143,844 A | 9/1992 | Abrahmsen et al. | |
| 6,399,750 B1 | 6/2002 | Johansson | |
| 8,592,555 B2 * | 11/2013 | Spector | 530/350 |
| 2006/0194950 A1 | 8/2006 | Hober et al. | |
| 2010/0221844 A1 * | 9/2010 | Bian et al. | 436/501 |

FOREIGN PATENT DOCUMENTS

| | | |
|---|---|---|
| CN | 101704879 | 5/2010 |
| EP | 1 123 389 | 10/2005 |
| EP | 1 992 692 A1 | 11/2008 |
| EP | 2 157 099 A1 | 2/2010 |
| JP | 2006-304633 | 11/2006 |
| JP | 2007-252368 | 10/2007 |
| JP | 2010-075175 | 4/2010 |
| WO | 00/69457 A1 | 11/2000 |
| WO | 03/080655 | 10/2003 |
| WO | 2008-039141 A1 | 4/2008 |

OTHER PUBLICATIONS

Tashiro, et al. Structures of bacterial immunoglobulin-binding domains and their complexes with immunoglobulins, Structural Biology, 1995, vol. 5, No. 4, pp. 471-481.
Hober, et al. Protein A chromatography for antibody purification, Journal of Chromatography B, Analyt. Technol. Biomed. Life Sci., 2007, vol. 848, No. 1, pp. 40-47.
Low, et al. Future of antibody purification, Journal of Chromatography B, 2007, vol. 848, pp. 48-63.
Roque, et al. Affinity-based methodologies and ligands for antibody purification: Advances and perspectives, Journal of Chromatography A, 2007, vol. 1160, pp. 44-55.
Nilsson, et al. A synthetic IgG-binding domain based on staphylococcal protein A, Protein Engineering, 1987, vol. 1, pp. 107-113.
Jansson, et al. All individual domains of staphylococcal protein A show Fab binding, FEMS Immunology and Medical Microbiology, 1998, vol. 20, pp. 69-78.
International Preliminary Report on Patentability for International Application No. PCT/JP2010/055030 mailed on Oct. 18, 2011.
International Search Report for International Application No. PCT/JP2010/055030 mailed on Jun. 22, 2010.
European Search Report for Application No. 10756084.9 Dated Apr. 29, 2013, 3 pgs.

\* cited by examiner

*Primary Examiner* — Brian J Gangle
(74) *Attorney, Agent, or Firm* — Amin, Turocy & Watson LLP

(57) ABSTRACT

An object of the present invention is to create a novel engineered Protein A ligand having better antibody dissociation properties in the presence of an acid than conventional engineered Protein A ligands and a further object of the present invention is to create a novel engineered Protein A ligand having higher alkali resistance. The present invention is to provide a protein having an affinity for an immunoglobulin, including an amino acid sequence derived from any of E, D, A, B and C domains of Protein A, wherein at least one Gly residue in the amino acid sequence is replaced with an amino acid other than Ala, and the protein has a lower affinity for an Fab region of an immunoglobulin than a protein including an amino acid sequence in which the Gly residue is replaced with Ala. Also, the present invention is to provide the protein having an affinity for an immunoglobulin, which has improved chemical stability in an alkaline condition compared to the corresponding domain.

27 Claims, 6 Drawing Sheets

FIG.1

|   | 1 | 10 | 20 | 30 | 40 | 50 |
|---|---|---|---|---|---|---|
| E | AQHDEA------QV-N------NAD---------------Q-ANV-G---Q------S------ |
| D | ADAQQ------D--S------NM----N-----------------Q-TNV-G---------ES------ |
| A | ------N--------N--------NM----N-----------------Q-ANL------------ES------ |
| B | ----------------------------N----------------Q-ANL-------------- |
| C | ADNKFNKEQQNAFYEILHLPNLTEEQRNGFIQSLKDDPSVSKEILAEAKKLNDAQAPK |

FIG.5

```
  1 GCAGATAACAAATTTAACAAAGAACAACAAAACGCTTTCTACGAAATCCTGCACTTGCCA  60
  1 GCTGATAACAAATTCAACAAAGAACAACAAAACGCTTTTTTATGAAATCCTTCACCTGCCA  60
  1 GCTGATAATAAATTCAACAAAGAACAACAAAATGCATTCTACGAAATCTTGCACCTTCCT  60
  1 GCAGACAACAAATTCAATAAGGAACAGCAAAACGCGTTTTATGAAATTCTGCATCTTCCA  60
  1 GCGGATAACAAGTTTAACAAAGAACAACAAAATGCTTTCTACGAGATCTTGCACCTTCCG  60

61 AACCTTACTGAAGAACAACGTAATGTTTTCATCCAATCCCTGAAAGATGATCCATCTGTA 120
 61 AATCTTACAGAAGAACAACGCAACGTATTCATTCAAAGCTTGAAGGATGACCCTTCCGTT 120
 61 AACCTGACTGAAGAGCAGCGTAACGTTTTTATCCAGAGCTTGAAAGACGATCCATCTGTC 120
 61 AACTTGACAGAGGAACAACGCAATGTTTTCATCCAATCCCTGAAAGATGATCCGAGCGTT 120
 61 AACCTGACTGAAGAACAACGTAACGTATTTATTCAGTCTTTGAAGGATGACCCATCCGTA 120

121 TCCAAAGAAATTTTTGGCAGAGGCTAAAAAACTTAACGACGCTCAGGCGCCTAAG       174
121 AGCAAAGAGATCCTGGCTGAAGCAAAAAAGTTGAATGATGCGCAAGCACCAAAA        174
121 TCCAAAGAAATTCTCGCAGAAGCGAAGAAACTGAACGATGCTCAAGCTCCGAAA        174
121 TCTAAGGAAATCTTTGGCTGAAGCAAAAAAACTGAACGACGCTCAAGCTCCAAAA       174
121 AGCAAAGAGATCCTGGCAGAAGCTAAAAAATTGAATGATGCACAAGCTCCAAAA        174
```

FIG.6
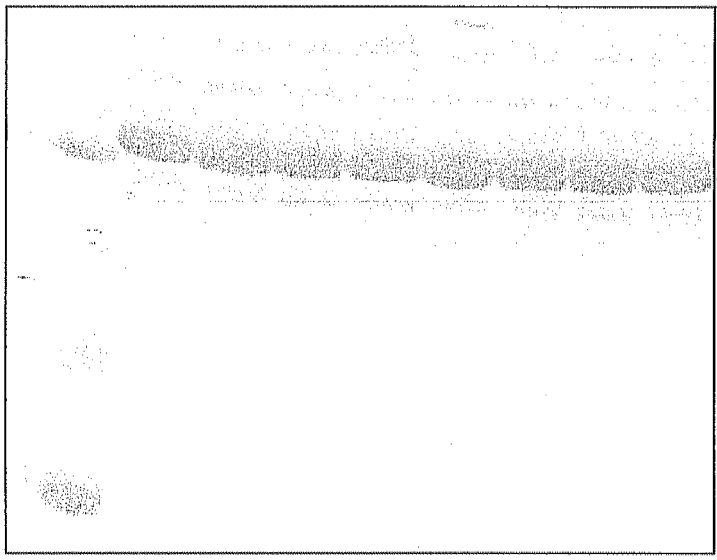
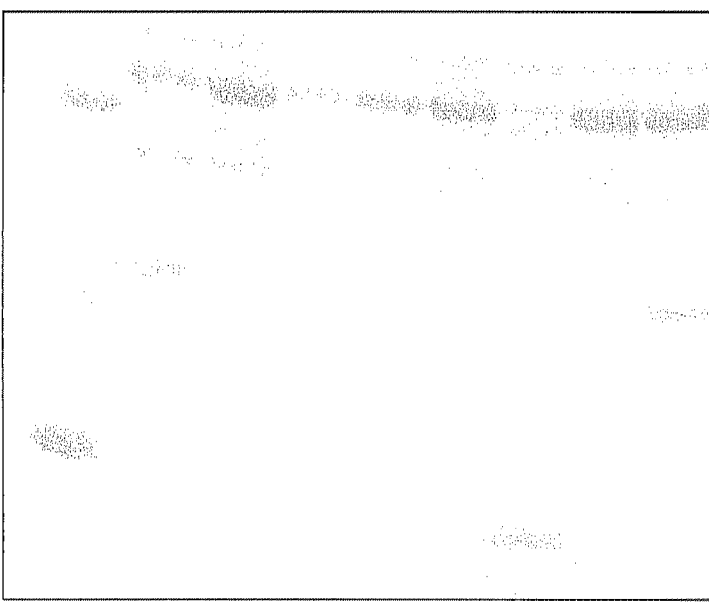

FIG.7
A
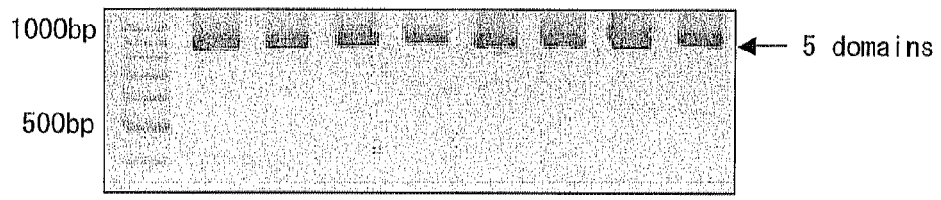
B
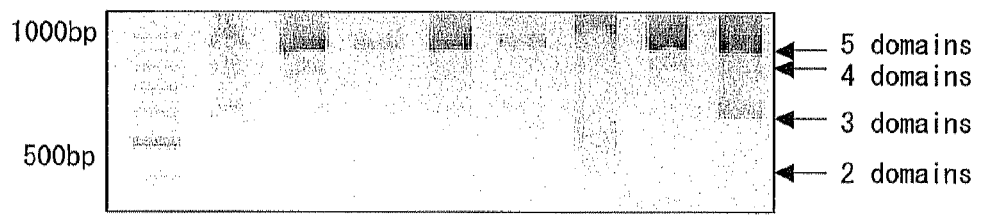

SEQUENCE LISTING

```
<160> NUMBER OF SEQ ID NOS: 107

<210> SEQ ID NO 1
<211> LENGTH: 56
<212> TYPE: PRT
<213> ORGANISM: Staphylococcus aureus

<400> SEQUENCE: 1

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 2
<211> LENGTH: 61
<212> TYPE: PRT
<213> ORGANISM: Staphylococcus aureus

<400> SEQUENCE: 2

Ala Asp Ala Gln Gln Asn Lys Phe Asn Lys Asp Gln Gln Ser Ala Phe
1               5                   10                  15

Tyr Glu Ile Leu Asn Met Pro Asn Leu Asn Glu Glu Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 3
<211> LENGTH: 58
<212> TYPE: PRT
<213> ORGANISM: Staphylococcus aureus

<400> SEQUENCE: 3

Ala Asp Asn Asn Phe Asn Lys Glu Gln Gln Asn Ala Phe Tyr Glu Ile
1               5                   10                  15
```

```
Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Glu Ser Gln Ala Pro Lys
    50                  55

<210> SEQ ID NO 4
<211> LENGTH: 58
<212> TYPE: PRT
<213> ORGANISM: Staphylococcus aureus

<400> SEQUENCE: 4

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 5
<211> LENGTH: 58
<212> TYPE: PRT
<213> ORGANISM: Staphylococcus aureus

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 6
<211> LENGTH: 58
<212> TYPE: PRT
<213> ORGANISM: Unknown
<220> FEATURE:
<223> OTHER INFORMATION: C-wild mutant

<400> SEQUENCE: 6

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Val Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 7
<211> LENGTH: 58
<212> TYPE: PRT
<213> ORGANISM: Unknown
<220> FEATURE:
<223> OTHER INFORMATION: C-wild mutant
```

<400> SEQUENCE: 7

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Leu Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 8
<211> LENGTH: 58
<212> TYPE: PRT
<213> ORGANISM: Unknown
<220> FEATURE:
<223> OTHER INFORMATION: C-wild mutant

<400> SEQUENCE: 8

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ile Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 9
<211> LENGTH: 58
<212> TYPE: PRT
<213> ORGANISM: Unknown
<220> FEATURE:
<223> OTHER INFORMATION: C-wild mutant

<400> SEQUENCE: 9

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Tyr Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 10
<211> LENGTH: 58
<212> TYPE: PRT
<213> ORGANISM: Unknown
<220> FEATURE:
<223> OTHER INFORMATION: C-wild mutant

<400> SEQUENCE: 10

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Phe Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys

```
                50                  55

<210> SEQ ID NO 11
<211> LENGTH: 58
<212> TYPE: PRT
<213> ORGANISM: Unknown
<220> FEATURE:
<223> OTHER INFORMATION: C-wild mutant

<400> SEQUENCE: 11

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Thr Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
        50                  55

<210> SEQ ID NO 12
<211> LENGTH: 58
<212> TYPE: PRT
<213> ORGANISM: Unknown
<220> FEATURE:
<223> OTHER INFORMATION: C-wild mutant

<400> SEQUENCE: 12

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Trp Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
        50                  55

<210> SEQ ID NO 13
<211> LENGTH: 58
<212> TYPE: PRT
<213> ORGANISM: Unknown
<220> FEATURE:
<223> OTHER INFORMATION: C-wild mutant

<400> SEQUENCE: 13

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Asp Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
        50                  55

<210> SEQ ID NO 14
<211> LENGTH: 58
<212> TYPE: PRT
<213> ORGANISM: Unknown
<220> FEATURE:
<223> OTHER INFORMATION: C-wild mutant

<400> SEQUENCE: 14

Ala Asp Asn Lys Phe Asn Lys Glu Gln Gln Asn Ala Phe Tyr Glu Ile
```

-continued

```
                1               5                  10                  15
Leu His Leu Pro Asn Leu Thr Glu Glu Gln Arg Asn Glu Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 15
<211> LENGTH: 58
<212> TYPE: PRT
<213> ORGANISM: Unknown
<220> FEATURE:
<223> OTHER INFORMATION: C-wild mutant

<400> SEQUENCE: 15

Ala Asp Asn Lys Phe Asn Lys Glu Gln Gln Asn Ala Phe Tyr Glu Ile
1               5                  10                  15

Leu His Leu Pro Asn Leu Thr Glu Glu Gln Arg Asn Arg Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 16
<211> LENGTH: 58
<212> TYPE: PRT
<213> ORGANISM: Unknown
<220> FEATURE:
<223> OTHER INFORMATION: C-wild mutant

<400> SEQUENCE: 16

Ala Asp Asn Lys Phe Asn Lys Glu Gln Gln Asn Ala Phe Tyr Glu Ile
1               5                  10                  15

Leu His Leu Pro Asn Leu Thr Glu Glu Gln Arg Asn His Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 17
<211> LENGTH: 58
<212> TYPE: PRT
<213> ORGANISM: Unknown
<220> FEATURE:
<223> OTHER INFORMATION: C-wild mutant

<400> SEQUENCE: 17

Ala Asp Asn Lys Phe Asn Lys Glu Gln Gln Asn Ala Phe Tyr Glu Ile
1               5                  10                  15

Leu His Leu Pro Asn Leu Thr Glu Glu Gln Arg Asn Met Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 18
```

```
<211> LENGTH: 58
<212> TYPE: PRT
<213> ORGANISM: Unknown
<220> FEATURE:
<223> OTHER INFORMATION: C-wild mutant

<400> SEQUENCE: 18

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ser Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 19
<211> LENGTH: 21
<212> TYPE: DNA
<213> ORGANISM: Unknown
<220> FEATURE:
<223> OTHER INFORMATION: synthetic oligonucleotide (DNA primer)

<400> SEQUENCE: 19
cgtggatccg ctgacaacaa a                                            21

<210> SEQ ID NO 20
<211> LENGTH: 30
<212> TYPE: DNA
<213> ORGANISM: Unknown
<220> FEATURE:
<223> OTHER INFORMATION: synthetic oligonucleotide (DNA primer)

<400> SEQUENCE: 20
agcagaattc taacattttg gtgcttgagc                                   30

<210> SEQ ID NO 21
<211> LENGTH: 174
<212> TYPE: DNA
<213> ORGANISM: Unknown
<220> FEATURE:
<223> OTHER INFORMATION: DNA code

<400> SEQUENCE: 21
gctgacaaca aattcaacaa agaacaacaa aatgctttct atgaaatttt acatttacct    60
aacttaactg aagaacaacg taacggcttc atccaaagcc ttaaagacga tccttcagtg   120
agcaaagaaa ttttagcaga agctaaaaag ctaaacgatg ctcaagcacc aaaa         174

<210> SEQ ID NO 22
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 22
cctaacttaa atgaagaaca acg                                          23

<210> SEQ ID NO 23
<211> LENGTH: 23
<212> TYPE: DNA
<213> ORGANISM: Unknown
<220> FEATURE:
<223> OTHER INFORMATION: synthetic oligonucleotide (DNA primer)
```

<400> SEQUENCE: 23
cgttgttctt catttaagtt agg    23

<210> SEQ ID NO 24
<211> LENGTH: 38
<212> TYPE: DNA
<213> ORGANISM: Unknown
<220> FEATURE:
<223> OTHER INFORMATION: synthetic oligonucleotide (DNA primer)

<400> SEQUENCE: 24
gacgatcctt cacagagcgc aaaccttta gcagaagc    38

<210> SEQ ID NO 25
<211> LENGTH: 38
<212> TYPE: DNA
<213> ORGANISM: Unknown
<220> FEATURE:
<223> OTHER INFORMATION: synthetic oligonucleotide (DNA primer)

<400> SEQUENCE: 25
gcttctgcta aaggtttgc gctctgtgaa ggatcgtc    38

<210> SEQ ID NO 26
<211> LENGTH: 174
<212> TYPE: DNA
<213> ORGANISM: Unknown
<220> FEATURE:
<223> OTHER INFORMATION: DNA code

<400> SEQUENCE: 26
gctgacaaca aattcaacaa agaacaacaa aatgctttct atgaaatttt acatttacct    60
aacttaaatg aagaacaacg taacggcttc atccaaagcc ttaaagacga tccttcacag   120
agcgcaaacc ttttagcaga agctaaaaag ctaaacgatg ctcaagcacc aaaa          174

<210> SEQ ID NO 27
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 27
caacgtaacg tgttcatcca aag    23

<210> SEQ ID NO 28
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 28
ctttggatga acacgttacg ttg    23

<210> SEQ ID NO 29
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 29
caacgtaacc tgttcatcca aag								23

<210> SEQ ID NO 30
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 30
ctttggatga acaggttacg ttg								23

<210> SEQ ID NO 31
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 31
caacgtaaca tcttcatcca aag								23

<210> SEQ ID NO 32
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 32
ctttggatga agatgttacg ttg								23

<210> SEQ ID NO 33
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 33
caacgtaact acttcatcca aag								23

<210> SEQ ID NO 34
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 34
ctttggatga agtagttacg ttg								23

<210> SEQ ID NO 35
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 35
caacgtaact tcttcatcca aag								23

<210> SEQ ID NO 36
<211> LENGTH: 23
<212> TYPE: DNA
<213> ORGANISM: Unknown

```
<220> FEATURE:
<223> OTHER INFORMATION: synthetic oligonucleotide (DNA primer)

<400> SEQUENCE: 36
ctttggatga agaagttacg ttg                                              23

<210> SEQ ID NO 37
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 37
caacgtaaca ccttcatcca aag                                              23

<210> SEQ ID NO 38
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 38
ctttggatga aggtgttacg ttg                                              23

<210> SEQ ID NO 39
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 39
caacgtaact ggttcatcca aag                                              23

<210> SEQ ID NO 40
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 40
ctttggatga accagttacg ttg                                              23

<210> SEQ ID NO 41
<211> LENGTH: 19
<212> TYPE: DNA
<213> ORGANISM: Unknown
<220> FEATURE:
<223> OTHER INFORMATION: synthetic oligonucleotide (DNA primer)

<400> SEQUENCE: 41
caacgtaaca gcttcatcc                                                   19

<210> SEQ ID NO 42
<211> LENGTH: 19
<212> TYPE: DNA
<213> ORGANISM: Unknown
<220> FEATURE:
<223> OTHER INFORMATION: synthetic oligonucleotide (DNA primer)

<400> SEQUENCE: 42
ggatgaagct gttacgttg                                                   19
```

<210> SEQ ID NO 43
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 43
caacgtaacg acttcatcca aag                                              23

<210> SEQ ID NO 44
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 44
ctttggatga agtcgttacg ttg                                              23

<210> SEQ ID NO 45
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 45
caacgtaacg aattcatcca aag                                              23

<210> SEQ ID NO 46
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 46
ctttggatga attcgttacg ttg                                              23

<210> SEQ ID NO 47
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 47
caacgtaacc gcttcatcca aag                                              23

<210> SEQ ID NO 48
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 48
ctttggatga agcggttacg ttg                                              23

<210> SEQ ID NO 49
<211> LENGTH: 23
<212> TYPE: DNA
<213> ORGANISM: Unknown
<220> FEATURE:
<223> OTHER INFORMATION: synthetic oligonucleotide (DNA primer)

-continued

<210> SEQ ID NO 49

```
<400> SEQUENCE: 49
caacgtaacc acttcatcca aag                                              23

<210> SEQ ID NO 50
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 50
ctttggatga agtggttacg ttg                                              23

<210> SEQ ID NO 51
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 51
caacgtaaca tgttcatcca aag                                              23

<210> SEQ ID NO 52
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 52
ctttggatga acatgttacg ttg                                              23

<210> SEQ ID NO 53
<211> LENGTH: 58
<212> TYPE: PRT
<213> ORGANISM: Unknown
<220> FEATURE:
<223> OTHER INFORMATION: B-wild mutant

<400> SEQUENCE: 53
```

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Val Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 54
<211> LENGTH: 58
<212> TYPE: PRT
<213> ORGANISM: Unknown
<220> FEATURE:
<223> OTHER INFORMATION: B-wild mutant

<400> SEQUENCE: 54
```

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Arg Phe Ile Gln
            20                  25                  30

```
Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 55
<211> LENGTH: 58
<212> TYPE: PRT
<213> ORGANISM: Unknown
<220> FEATURE:
<223> OTHER INFORMATION: B-wild mutant

<400> SEQUENCE: 55

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Asp Phe Ile Gln
            20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 56
<211> LENGTH: 58
<212> TYPE: PRT
<213> ORGANISM: Unknown
<220> FEATURE:
<223> OTHER INFORMATION: B-wild mutant

<400> SEQUENCE: 56

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Trp Phe Ile Gln
            20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 57
<211> LENGTH: 290
<212> TYPE: PRT
<213> ORGANISM: Staphylococcus aureus

<400> SEQUENCE: 57

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Val Phe Ile Gln
            20                  25                  30

Ser Leu Lys Asp Asp Pro Ser Val Ser Lys Glu Ile Leu Ala Glu Ala
            35                  40                  45

Lys Lys Leu Asn Asp Ala Gln Ala Pro Lys Ala Asp Asn Lys Phe Asn
        50                  55                  60

Lys Glu Gln Gln Asn Ala Phe Tyr Glu Ile Leu His Leu Pro Asn Leu
65                  70                  75                  80

Thr Glu Glu Gln Arg Asn Val Phe Ile Gln Ser Leu Lys Asp Asp Pro
                85                  90                  95

Ser Val Ser Lys Glu Ile Leu Ala Glu Ala Lys Lys Leu Asn Asp Ala
                100                 105                 110
```

Gln Ala Pro Lys Ala Asp Asn Lys Phe Asn Lys Glu Gln Gln Asn Ala
            115                 120                 125

Phe Tyr Glu Ile Leu His Leu Pro Asn Leu Thr Glu Glu Gln Arg Asn
        130                 135                 140

Val Phe Ile Gln Ser Leu Lys Asp Asp Pro Ser Val Ser Lys Glu Ile
145                 150                 155                 160

Leu Ala Glu Ala Lys Lys Leu Asn Asp Ala Gln Ala Pro Lys Ala Asp
                165                 170                 175

Asn Lys Phe Asn Lys Glu Gln Gln Asn Ala Phe Tyr Glu Ile Leu His
            180                 185                 190

Leu Pro Asn Leu Thr Glu Glu Gln Arg Asn Val Phe Ile Gln Ser Leu
        195                 200                 205

Lys Asp Asp Pro Ser Val Ser Lys Glu Ile Leu Ala Glu Ala Lys Lys
    210                 215                 220

Leu Asn Asp Ala Gln Ala Pro Lys Ala Asp Asn Lys Phe Asn Lys Glu
225                 230                 235                 240

Gln Gln Asn Ala Phe Tyr Glu Ile Leu His Leu Pro Asn Leu Thr Glu
                245                 250                 255

Glu Gln Arg Asn Val Phe Ile Gln Ser Leu Lys Asp Asp Pro Ser Val
            260                 265                 270

Ser Lys Glu Ile Leu Ala Glu Ala Lys Lys Leu Asn Asp Ala Gln Ala
        275                 280                 285

Pro Lys
    290

<210> SEQ ID NO 58
<211> LENGTH: 881
<212> TYPE: DNA
<213> ORGANISM: Unknown
<220> FEATURE:
<223> OTHER INFORMATION: synthetic DNA

<400> SEQUENCE: 58
ctgcagataa caaatttaac aaagaacaac aaaacgcttt ctacgaaatc ctgcacttgc      60
caaaccttac tgaagaacaa cgtaatgttt catccaatc cctgaaagat gatccatctg     120
tatccaaaga aattttggca gaggctaaaa aacttaacga cgctcaggcg cctaaggctg     180
ataacaaatt caacaagaa caacaaaacg cttttatga atccttcac ctgccaaatc      240 ttacagaaga acaacgcaac gtattcattc aaagcttgaa ggatgaccct tccgttagca     300
aagagatcct ggctgaagca aaaaagttga atgatgcgca agcaccaaaa gctgataata     360
aattcaacaa gaacaacaa aatgcattct acgaaatctt gccacttcct aacctgactg     420
aagagcagcg taacgttttt atccagagct gaaagacga tccatctgtc tccaaagaaa     480
ttctcgcaga agcgaagaaa ctgaacgatg ctcaagctcc gaaagcagac aacaaattca     540
ataaggaaca gcaaaacgcg ttttatgaaa ttctgcatct tccaaacttg acagaggaac     600
aacgcaatgt tttcatccaa tccctgaaag atgatccgag cgtttctaag gaaatcttgg     660
ctgaagcaaa aaactgaac gacgctcaag ctccaaaagc ggataacaag tttaacaaag     720 aacaacaaa tgcttctac gagatcttgc accttccgaa cctgactgaa gaacaacgta     780
acgtatttat tcagtctttg aaggatgacc catccgtaag caaagagatc ctggcagaag     840
ctaaaaaatt gaatgatgca caagctccaa ataatctag a                         881

<210> SEQ ID NO 59
<211> LENGTH: 172

```
<212> TYPE: DNA
<213> ORGANISM: Unknown
<220> FEATURE:
<223> OTHER INFORMATION: synthetic DNA

<400> SEQUENCE: 59
ctgcagataa caaatttaac aaagaacaac aaaacgcttt ctacgaaatc ctgcacttgc      60
caaaccttac tgaagaacaa cgtaatgttt tcatccaatc cctgaaagat gatccatctg     120
tatccaaaga aattttggca gaggctaaaa aacttaacga cgctcaggcg cc             172

<210> SEQ ID NO 60
<211> LENGTH: 111
<212> TYPE: DNA
<213> ORGANISM: Unknown
<220> FEATURE:
<223> OTHER INFORMATION: synthetic DNA

<400> SEQUENCE: 60
ggcgcctaag gctgataaca aattcaacaa agaacaacaa aacgcttttt atgaaatcct      60
tcacctgcca aatcttacag aagaacaacg caacgtattc attcaaagct t              111

<210> SEQ ID NO 61
<211> LENGTH: 290
<212> TYPE: DNA
<213> ORGANISM: Unknown
<220> FEATURE:
<223> OTHER INFORMATION: synthetic DNA

<400> SEQUENCE: 61
aagcttgaag gatgacccct ccgttagcaa agagatcctg gctgaagcaa aaagttgaa       60 tgatgcgcaa gcaccaaaag ctgataataa attcaacaaa gaacaacaaa atgcattcta     120
cgaaatcttg caccttccta acctgactga agagcagcgt aacgttttta tccagagctt     180
gaaagacgat ccatctgtct ccaaagaaat tctcgcagaa gcgaagaaac tgaacgatgc     240
tcaagctccg aaagcagaca acaaattcaa taaggaacag caaaacgcgt                290

<210> SEQ ID NO 62
<211> LENGTH: 192
<212> TYPE: DNA
<213> ORGANISM: Unknown
<220> FEATURE:
<223> OTHER INFORMATION: synthetic DNA

<400> SEQUENCE: 62
acgcgtttta tgaaattctg catcttccaa acttgacaga ggaacaacgc aatgttttca      60
tccaatccct gaaagatgat ccgagcgttt ctaaggaaat cttggctgaa gcaaaaaaac     120
tgaacgacgc tcaagctcca aaagcggata acaagtttaa caagaacaa caaatgcttt      180 tctacgagat ct                                                         192

<210> SEQ ID NO 63
<211> LENGTH: 140
<212> TYPE: DNA
<213> ORGANISM: Unknown
<220> FEATURE:
<223> OTHER INFORMATION: synthetic DNA

<400> SEQUENCE: 63
agatcttgca ccttccgaac ctgactgaag aacaacgtaa cgtatttatt cagtctttga      60
aggatgaccc atccgtaagc aaagagatcc tggcagaagc taaaaaattg aatgatgcac     120
```
aagctccaaa ataatctaga                                              140

<210> SEQ ID NO 64
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 64
acaacgtaat tggttcatcc aat                                          23

<210> SEQ ID NO 65
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 65
attggatgaa ccaattacgt tgt                                          23

<210> SEQ ID NO 66
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 66
acaacgcaac tggttcattc aaa                                          23

<210> SEQ ID NO 67
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 67
tttgaatgaa ccagttgcgt tgt                                          23

<210> SEQ ID NO 68
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 68
gcagcgtaac tggtttatcc aga                                          23

<210> SEQ ID NO 69
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 69
tctggataaa ccagttacgc tgc                                          23

<210> SEQ ID NO 70
<211> LENGTH: 23
<212> TYPE: DNA
<213> ORGANISM: Unknown

```
<220> FEATURE:
<223> OTHER INFORMATION: synthetic oligonucleotide (DNA primer)

<400> SEQUENCE: 70
acaacgcaat tggttcatcc aat                                              23

<210> SEQ ID NO 71
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 71
attggatgaa ccaattgcgt tgt                                              23

<210> SEQ ID NO 72
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 72
acaacgtaac tggtttattc agt                                              23

<210> SEQ ID NO 73
<211> LENGTH: 23
<212> TYPE: DNA
<213> ORGANISM: Unknown
<220> FEATURE:
<223> OTHER INFORMATION: synthetic oligonucleotide (DNA primer)

<400> SEQUENCE: 73
actgaataaa ccagttacgt tgt                                              23

<210> SEQ ID NO 74
<211> LENGTH: 172
<212> TYPE: DNA
<213> ORGANISM: Unknown
<220> FEATURE:
<223> OTHER INFORMATION: synthetic DNA

<400> SEQUENCE: 74
ctgcagataa caaatttaac aaagaacaac aaaacgcttt ctacgaaatc ctgcacttgc      60
caaaccttac tgaagaacaa cgtaattggt tcatccaatc cctgaaagat gatccatctg     120
tatccaaaga aattttggca gaggctaaaa aacttaacga cgctcaggcg cc            172

<210> SEQ ID NO 75
<211> LENGTH: 111
<212> TYPE: DNA
<213> ORGANISM: Unknown
<220> FEATURE:
<223> OTHER INFORMATION: synthetic DNA

<400> SEQUENCE: 75
ggcgcctaag gctgataaca aattcaacaa agaacaacaa aacgcttttt atgaaatcct      60
tcacctgcca aatcttacag aagaacaacg caactggttc attcaaagct t             111

<210> SEQ ID NO 76
<211> LENGTH: 290
<212> TYPE: DNA
<213> ORGANISM: Unknown
<220> FEATURE:
```

<223> OTHER INFORMATION: synthetic DNA

<400> SEQUENCE: 76

```
aagcttgaag gatgacccttt ccgttagcaa agagatcctg gctgaagcaa aaaagttgaa      60
tgatgcgcaa gcaccaaaag ctgataataa attcaacaaa gaacaacaaa atgcattcta     120
cgaaatcttg caccttccta acctgactga agagcagcgt aactggttta tccagagctt     180
gaaagacgat ccatctgtct ccaaagaaat tctcgcagaa gcgaagaaac tgaacgatgc     240
tcaagctccg aaagcagaca acaaattcaa taaggaacag caaaacgcgt                290
```

<210> SEQ ID NO 77
<211> LENGTH: 192
<212> TYPE: DNA
<213> ORGANISM: Unknown
<220> FEATURE:
<223> OTHER INFORMATION: synthetic DNA

<400> SEQUENCE: 77

```
acgcgtttta tgaaattctg catcttccaa acttgacaga ggaacaacgc aattggttca      60
tccaatccct gaaagatgat ccgagcgttt ctaaggaaat cttggctgaa gcaaaaaaac     120
tgaacgacgc tcaagctcca aaagcggata caagtttaa caagaacaa caaatgctt       180
tctacgagat ct                                                        192
```

<210> SEQ ID NO 78
<211> LENGTH: 140
<212> TYPE: DNA
<213> ORGANISM: Unknown
<220> FEATURE:
<223> OTHER INFORMATION: synthetic DNA

<400> SEQUENCE: 78

```
agatcttgca ccttccgaac ctgactgaag aacaacgtaa ctggtttatt cagtctttga      60
aggatgaccc atccgtaagc aaagagatcc tggcagaagc taaaaaattg aatgatgcac     120
aagctccaaa ataatctaga                                                140
```

<210> SEQ ID NO 79
<211> LENGTH: 881
<212> TYPE: DNA
<213> ORGANISM: Unknown
<220> FEATURE:
<223> OTHER INFORMATION: synthetic DNA

<400> SEQUENCE: 79

```
ctgcagataa caaatttaac aaagaacaac aaaacgcttt ctacgaaatc ctgcacttgc      60
caaaccttac tgaagaacaa cgtaattggt tcatccaatc cctgaaagat gatccatctg     120
tatccaaaga aatttttggca gaggctaaaa aacttaacga cgctcaggcg cctaaggctg    180
ataacaaatt caacaagaa caacaaaacg ctttttatga atccttcac ctgccaaatc      240
ttacagaaga acaacgcaac tggttcattc aaagcttgaa ggatgaccct tccgttagca     300
aagagatcct ggctgaagca aaaagttga atgatgcgca agcaccaaaa gctgataata     360
aattcaacaa agaacaacaa aatgcattct acgaaatctt gcaccttcct aacctgactg     420
aagagcagcg taactggttt atccagagct tgaaagacga tccatctgtc tccaaagaaa     480
ttctcgcaga agcgaagaaa ctgaacgatg ctcaagctcc gaaagcagac aacaaattca     540
ataaggaaca gcaaaacgcg ttttatgaaa ttctgcatct tccaaacttg acagaggaac     600
aacgcaattg gttcatccaa tccctgaaag atgatccgag cgtttctaag gaaatcttgg     660
```
ctgaagcaaa aaaactgaac gacgctcaag ctccaaaagc ggataacaag tttaacaaag    720
aacaacaaaa tgctttctac gagatcttgc accttccgaa cctgactgaa gaacaacgta    780
actggtttat tcagtctttg aaggatgacc catccgtaag caaagagatc ctggcagaag    840
ctaaaaaatt gaatgatgca caagctccaa aataatctag a    881

<210> SEQ ID NO 80
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 80
acaacgtaat tatttcatcc aatcc    25

<210> SEQ ID NO 81
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 81
attggatgaa ataattacgt tgttc    25

<210> SEQ ID NO 82
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 82
acaacgcaac tacttcattc aaagc    25

<210> SEQ ID NO 83
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 83
tttgaatgaa gtagttgcgt tgttc    25

<210> SEQ ID NO 84
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 84
gcagcgtaac tattttatcc agagc    25

<210> SEQ ID NO 85
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 85
tctggataaa atagttacgc tgctc                                          25

<210> SEQ ID NO 86
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 86
acaacgcaat tatttcatcc aatcc                                          25

<210> SEQ ID NO 87
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 87
attggatgaa ataattgcgt tgttc                                          25

<210> SEQ ID NO 88
<211> LENGTH: 24
<212> TYPE: DNA
<213> ORGANISM: Unknown
<220> FEATURE:
<223> OTHER INFORMATION: synthetic oligonucleotide (DNA primer)

<400> SEQUENCE: 88
acaacgtaac tactttattc agtc                                           24

<210> SEQ ID NO 89
<211> LENGTH: 25
<212> TYPE: DNA
<213> ORGANISM: Unknown
<220> FEATURE:
<223> OTHER INFORMATION: synthetic oligonucleotide (DNA primer)

<400> SEQUENCE: 89
actgaataaa gtagttacgt tgttc                                          25

<210> SEQ ID NO 90
<211> LENGTH: 172
<212> TYPE: DNA
<213> ORGANISM: Unknown
<220> FEATURE:
<223> OTHER INFORMATION: synthetic DNA

<400> SEQUENCE: 90
ctgcagataa caaatttaac aaagaacaac aaaacgcttt ctacgaaatc ctgcacttgc     60
caaaccttac tgaagaacaa cgtaattatt tcatccaatc cctgaaagat gatccatctg    120
tatccaaaga aattttggca gaggctaaaa aacttaacga cgctcaggcg cc            172

<210> SEQ ID NO 91
<211> LENGTH: 111
<212> TYPE: DNA
<213> ORGANISM: Unknown
<220> FEATURE:
<223> OTHER INFORMATION: synthetic DNA

<400> SEQUENCE: 91
ggcgcctaag gctgataaca aattcaacaa agaacaacaa aacgcttttt atgaaatcct     60
tcacctgcca aatcttacag aagaacaacg caactacttc attcaaagct t             111

<210> SEQ ID NO 92
<211> LENGTH: 290
<212> TYPE: DNA
<213> ORGANISM: Unknown
<220> FEATURE:
<223> OTHER INFORMATION: synthetic DNA

<400> SEQUENCE: 92

```
aagcttgaag gatgacccttt ccgttagcaa agagatcctg gctgaagcaa aaaagttgaa    60
tgatgcgcaa gcaccaaaag ctgataataa attcaacaaa gaacaacaaa atgcattcta   120
cgaaatcttg caccttccta acctgactga agagcagcgt aactatttta tccagagctt   180
gaaagacgat ccatctgtct ccaaagaaat tctcgcagaa gcgaagaaac tgaacgatgc   240
tcaagctccg aaagcagaca acaaattcaa taaggaacag caaaacgcgt             290
```

<210> SEQ ID NO 93
<211> LENGTH: 192
<212> TYPE: DNA
<213> ORGANISM: Unknown
<220> FEATURE:
<223> OTHER INFORMATION: synthetic DNA

<400> SEQUENCE: 93

```
acgcgtttta tgaaattctg catcttccaa acttgacaga ggaacaacgc aattatttca    60
tccaatccct gaaagatgat ccgagcgttt ctaaggaaat cttggctgaa gcaaaaaaac   120
tgaacgacgc tcaagctcca aaagcggata acaagtttaa caagaacaa caaaatgctt   180
tctacgagat ct                                                        192
```

<210> SEQ ID NO 94
<211> LENGTH: 140
<212> TYPE: DNA
<213> ORGANISM: Unknown
<220> FEATURE:
<223> OTHER INFORMATION: synthetic DNA

<400> SEQUENCE: 94

```
agatcttgca ccttccgaac ctgactgaag aacaacgtaa ctactttatt cagtctttga    60
aggatgaccc atccgtaagc aaagagatcc tggcagaagc taaaaaattg aatgatgcac   120
aagctccaaa ataatctaga                                                140
```

<210> SEQ ID NO 95
<211> LENGTH: 881
<212> TYPE: DNA
<213> ORGANISM: Unknown
<220> FEATURE:
<223> OTHER INFORMATION: synthetic DNA

<400> SEQUENCE: 95

```
ctgcagataa caaatttaac aaagaacaac aaaacgcttt ctacgaaatc ctgcacttgc    60
caaaccttac tgaagaacaa cgtaattatt tcatccaatc cctgaaagat gatccatctg   120
tatccaaaga aatttttggca gaggctaaaa aacttaacga cgctcaggcg cctaaggctg   180
ataacaaatt caacaaagaa caacaaaacg ctttttatga aatccttcac ctgccaaatc   240
ttacagaaga acaacgcaac tacttcattc aaagcttgaa ggatgaccct tccgttagca   300
aagagatcct ggctgaagca aaaaagttga atgatgcgca agcaccaaaa gctgataata   360
aattcaacaa agaacaacaa aatgcattct acgaaatctt gcaccttcct aacctgactg   420
```

```
aagagcagcg taactatttt atccagagct tgaaagacga tccatctgtc tccaaagaaa    480
ttctcgcaga agcgaagaaa ctgaacgatg ctcaagctcc gaaagcagac aacaaattca    540
ataaggaaca gcaaaacgcg ttttatgaaa ttctgcatct tccaaacttg acagaggaac    600
aacgcaatta tttcatccaa tccctgaaag atgatccgag cgtttctaag gaaatcttgg    660
ctgaagcaaa aaaactgaac gacgctcaag ctccaaaagc ggataacaag tttaacaaag    720
aacaacaaaa tgctttctac gagatcttgc accttccgaa cctgactgaa gaacaacgta    780
actactttat tcagtctttg aaggatgacc catccgtaag caaagagatc ctggcagaag    840
ctaaaaaatt gaatgatgca caagctccaa ataatctag a                        881
```

<210> SEQ ID NO 96
<211> LENGTH: 19
<212> TYPE: DNA
<213> ORGANISM: Unknown
<220> FEATURE:
<223> OTHER INFORMATION: synthetic oligonucleotide (DNA primer)

<400> SEQUENCE: 96

```
caacgtaacg ccttcatcc                                                 19
```

<210> SEQ ID NO 97
<211> LENGTH: 19
<212> TYPE: DNA
<213> ORGANISM: Unknown
<220> FEATURE:
<223> OTHER INFORMATION: synthetic oligonucleotide (DNA primer)

<400> SEQUENCE: 97

```
ggatgaaggc gttacgttg                                                 19
```

<210> SEQ ID NO 98
<211> LENGTH: 58
<212> TYPE: PRT
<213> ORGANISM: Unknown
<220> FEATURE:
<223> OTHER INFORMATION: C-wild mutant

<400> SEQUENCE: 98

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 99
<211> LENGTH: 58
<212> TYPE: PRT
<213> ORGANISM: Unknown
<220> FEATURE:
<223> OTHER INFORMATION: B-wild mutant

<400> SEQUENCE: 99

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala

```
                35                  40                  45
Lys Lys Leu Asn Asp Ala Gln Ala Pro Lys
    50                  55

<210> SEQ ID NO 100
<211> LENGTH: 30
<212> TYPE: DNA
<213> ORGANISM: Unknown
<220> FEATURE:
<223> OTHER INFORMATION: synthetic oligonucleotide (DNA primer)

<400> SEQUENCE: 100
agcaccaaaa gctgacaaca aattcaacaa                               30

<210> SEQ ID NO 101
<211> LENGTH: 29
<212> TYPE: DNA
<213> ORGANISM: Unknown
<220> FEATURE:
<223> OTHER INFORMATION: synthetic oligonucleotide (DNA primer)

<400> SEQUENCE: 101
cccaagcttt ggatgaagcc gttacgttg                                29

<210> SEQ ID NO 102
<211> LENGTH: 34
<212> TYPE: DNA
<213> ORGANISM: Unknown
<220> FEATURE:
<223> OTHER INFORMATION: synthetic oligonucleotide (DNA primer)

<400> SEQUENCE: 102
cccaagcttg aaagacgatc cttcagtgag caaa                          34

<210> SEQ ID NO 103
<211> LENGTH: 27
<212> TYPE: DNA
<213> ORGANISM: Unknown
<220> FEATURE:
<223> OTHER INFORMATION: synthetic oligonucleotide (DNA primer)

<400> SEQUENCE: 103
tgttgtcagc ttttggtgct tgagcat                                  27

<210> SEQ ID NO 104
<211> LENGTH: 186
<212> TYPE: DNA
<213> ORGANISM: Staphylococcus aureus

<400> SEQUENCE: 104
cccaagcttg aaagacgatc cttcagtgag caaagaaatt ttagcagaag ctaaaaagct    60
aaacgatgct caagcaccaa agctgacaa caaattcaac aaagaacaac aaaatgcttt   120
ctatgaaatt ttacatttac ctaacttaac tgaagaacaa cgtaacggct tcatccaaag   180
cttggg                                                             186

<210> SEQ ID NO 105
<211> LENGTH: 43
<212> TYPE: DNA
<213> ORGANISM: Unknown
<220> FEATURE:
<223> OTHER INFORMATION: synthetic oligonucleotide (DNA primer)

<400> SEQUENCE: 105
```

```
ccgctcgagc catggctttc gctgctgaca acaaattcaa caa            43

<210> SEQ ID NO 106
<211> LENGTH: 34
<212> TYPE: DNA
<213> ORGANISM: Unknown
<220> FEATURE:
<223> OTHER INFORMATION: synthetic oligonucleotide (DNA primer)

<400> SEQUENCE: 106
cgggatcctt attattttgg tgcttgagca tcgt                      34

<210> SEQ ID NO 107
<211> LENGTH: 211
<212> TYPE: DNA
<213> ORGANISM: Staphylococcus aureus

<400> SEQUENCE: 107
ccgctcgagc catggctttc gctgctgaca acaaattcaa caaagaacaa caaaatgctt    60
tctatgaaat tttacattta cctaacttaa ctgaagaaca acgtaacggc ttcatccaaa   120
gcttgaaaga cgatccttca gtgagcaaag aaattttagc agaagctaaa aagctaaacg   180
atgctcaagc accaaaataa taaggatccc g                                  211
```

PROTEIN HAVING AFFINITY FOR IMMUNOGLOBULIN, AND IMMUNOGLOBULIN-BINDING AFFINITY LIGAND

TECHNICAL FIELD

The present invention relates to a protein that specifically binds to an antibody, an affinity separation matrix containing this protein as an immunoglobulin-binding affinity ligand, and a method for separating and purifying, or adsorbing and removing an antibody with the use of this matrix.

BACKGROUND ART

Antibodies specifically bind to substances called antigens, and detoxify and remove antigen-containing factors with the cooperation of other biomolecules and cells. The name "antibody" is particularly based on such a binding ability to an antigen, and these substances are known as "immunoglobulins".

Recent developments in genetic engineering, protein engineering, and cell technology have led to the accelerated development of antibody drugs, which refer to pharmaceuticals utilizing the abilities of antibodies. Since the antibody drugs more specifically attack a target molecule than conventional pharmaceuticals, use thereof is expected to further reduce side effects and to produce higher therapeutic effects. In fact, these drugs contribute to improvement in various disease conditions.

The quality of antibody drugs is thought to largely depend on the purity compared to the quality of other recombinant protein pharmaceuticals because the doses of these antibody drugs to the body are very large. In order to produce a high purity antibody, techniques using an adsorbing material that contains a molecule capable of specifically binding to an antibody as a ligand (e.g. affinity chromatography) are commonly employed.

Most of the antibody drugs developed so far are monoclonal IgG antibodies. These antibodies are mass produced by recombinant cell-culture technology or the like and purified using proteins having affinities for IgG antibodies. One well-known example of immunoglobulin-binding proteins having affinities for IgG antibodies is Protein A. Protein A is a cell wall protein produced by the gram-positive bacteria *Staphylococcus aureus* and contains a signal sequence S, five immunoglobulin-binding domains (E domain, D domain, A domain, B domain and C domain) and an XM region, which is a cell wall-anchoring domain (Non-Patent Document 1). In an initial purification process (capture process) in antibody drug manufacture, affinity chromatography columns that contain as a ligand Protein A immobilized on a water-insoluble carrier (hereinafter, referred to as protein A columns) are commonly used (Non-Patent Documents 1 to 3).

Various techniques for improving the performance of protein A columns have been developed. Various technological developments in ligands have also been made. Initially, wild-type protein A was used as a ligand, but currently a recombinant Protein A altered by protein engineering is used as a ligand in many techniques for improving the performance of columns.

Typical examples of such a recombinant Protein A include a recombinant Protein A without the XM region that does not bind to immunoglobulins (rProtein A Sepharose (trademark) available from GE health care, Japan). Currently, columns containing as a ligand a recombinant Protein A without the XM region are widely used for industrial purposes because these columns advantageously further reduce non-specific adsorption of proteins compared to conventional ones.

Further, the use of a recombinant Protein A containing a mutant Cys residue (Patent Document 1) or a recombinant Protein A containing a plurality of mutant Lys residues (Patent Document 2) as a ligand has also been proposed. These Protein A mutants are efficient in their immobilization on a water-insoluble carrier and have advantages in the antibody-binding capacity of columns and reduction in leakage of the immobilized ligands.

Also well known is a technique using, as a ligand of an engineered recombinant Protein A, an engineered domain obtained by introducing mutation into the B domain (this engineered domain is referred to as a Z domain) (Patent Document 3, and Non-patent Documents 1 and 4). Specifically, the Z domain is an engineered domain obtained by introducing a mutation to replace the Gly residue at position 29 of the B domain with Ala. Although, in the Z domain, the Ala residue at position 1 of the B domain is also replaced with Val, this mutation is intended to facilitate genetic engineering preparation of a gene encoding multiple connected domains and does not affect the domain functions (for example, a mutant in which the Val residue at position 1 of the Z domain is replaced with Ala is used in an example of Patent Document 4)

The Z domain is known to be more alkali resistant than the B domain and advantageously can be reused through alkali washing. Patent Documents 5 and 6 disclose a ligand derived from the Z domain in which an Asn residue is replaced with another amino acid so as to impart further higher alkali resistance, and this ligand is already used for the industrial purpose.

Another feature of the Z domain is its reduced binding ability to the Fab region of immunoglobulins (Non-Patent Document 5). This feature advantageously facilitates dissociation of an antibody binding to the Z domain using an acid (Non-Patent Document 1 and Patent Document 7).

In addition to the Z domain derived from the B domain, highly alkali-resistant engineered Protein A ligands derived from the C domain of Protein A have also been studied (Patent Document 4). These ligands characteristically take advantage of the inherent high alkali resistance of the wild-type C domain and have been receiving attentions as new alternative base domains to the Z domain. However, our studies on the C domain have revealed the disadvantage that it is difficult to dissociate an antibody binding to the C domain using an acid. The C domain, as taught in Non-Patent Document 2 and Patent Document 4, has strong binding ability to the Fab region of immunoglobulins, and this ability is presumably supposed to make it difficult to dissociate the antibody using an acid. In order to overcome this disadvantage, we examined a C-domain mutant in which the Gly residue at position 29 is replaced with Ala, for its antibody dissociation properties in the presence of an acid. The result revealed that the ability of the C domain mutant was improved over that of the wild-type C domain but was still not enough. The reason for this was revealed by an analysis of the interaction between the protein molecules, and specifically was that the C domain in which the Gly residue at position 29 was replaced with Ala did not have sufficiently reduced binding ability to the Fab region of immunoglobulins.

As described above, it is widely known that replacement of the Gly residues corresponding to position 29 in the immunoglobulin-binding domains (E, D, A, B and C domains) of Protein A with Ala is a useful mutation strategy. In fact, the technologies for engineered Protein A developed after the disclosure of the "G29A" mutations in 1987 include these mutations (Patent Documents 2, 4 and 6).

However, all these technologies teach only the G29A mutations, that is, replacement of the Gly residues corresponding to position 29 with Ala as mutations of the amino acid residues corresponding to position 29 in the immunoglobulin-binding domains of Protein A and are silent about a mutation to introduce an amino acid residue other than Ala into this position. The G29A mutations are designed to minimize the conformational change. In this strategy, Ala is regarded as the best amino acid because Ala has the second smallest side chain next to Gly. Replacement with an amino acid having a larger side chain has not been examined so far (Non-Patent Document 4). Accordingly, it was unclear whether replacement of the Gly residues corresponding to position 29 with an amino acid having a larger side chain than Ala, which would result in a larger conformational change and might impair the original abilities (e.g. binding ability to immunoglobulins), could produce a better effect than that achieved by the replacement with Ala. Although it is in 1987 (Non-Patent Document 4) when replacement of the Gly residues corresponding to position 29 with Ala was disclosed, replacement with an amino acid other than Ala has not been proposed so far.

Patent Document 1: U.S. Pat. No. 6,399,750
Patent Document 2: JP 2007-252368 A
Patent Document 3: U.S. Pat. No. 5,143,844
Patent Document 4: JP 2006-304633 A
Patent Document 5: EP 1123389
Patent Document 6: WO 03/080655
Patent Document 7: U.S. Patent Application No. 2006/0194950
Non-Patent Document 1: Hober S. et al., "J. Chromatogr. B" 2007, vol. 848, pages 40-47
Non-Patent Document 2: Low D. et al., "J. Chromatogr. B", 2007, vol. 848, pages 48-63
Non-Patent Document 3: Roque A. C. A. et al., "J. Chromatogr. A", 2007, vol. 1160, pages 44-55
Non-Patent Document 4: Nilsson B. et al., "Protein Engineering", 1987, vol. 1, pages 107-113
Non-Patent Document 5: Jansson B. et al., "FEMS Immunology and Medical Microbiology", 1998, vol. 20, pages 69-78

SUMMARY OF THE INVENTION

An object of the present invention is to develop an engineering technology for creating a novel engineered Protein A ligand having better antibody dissociation properties in the presence of an acid than conventional engineered Protein A ligands. A further object is to create a novel engineered Protein A ligand with higher alkali resistance.

In order to achieve the above objects, the present inventors constructed a large number of recombinant Protein A mutant molecules, recovered these mutants from transformants by protein engineering and genetic engineering techniques, and examined and compared the physical properties of these recovered mutants. As a result, the present inventors completed the present invention.

Specifically, the present invention relates to a protein having an affinity for an immunoglobulin, which includes an amino acid sequence derived from any of E, D, A, B and C domains of Protein A of SEQ ID NOs:1 to 5, wherein at least one Gly residue in the amino acid sequence is replaced with an amino acid other than Ala, and the protein has a lower affinity for an Fab region of an immunoglobulin than a protein including an amino acid sequence in which the Gly residue is replaced with Ala.

Preferably, the Gly residue is any of Gly residues corresponding to position 29 of the C domain, which are conserved in the E, D, A, B and C domains of Protein A.

Preferably, the Gly residues corresponding to position 29 of the C domain are a Gly residue at position 27 of the E domain, a Gly residue at position 32 of the D domain, a Gly residue at position 29 of the A domain, a Gly residue at position 29 of the B domain, and the Gly residue at position 29 of the C domain.

Preferably, the amino acid other than Ala is any of Val, Leu, Ile, Phe, Tyr, Trp, Thr, Asp, Glu, Arg, His, Lys, Met, Cys, Asn, and Gln.

Preferably, the amino acid other than Ala is any of Leu, Ile, Phe, Tyr, Trp, Glu, Arg, and Met.

Preferably, an amino acid sequence before introduction of the mutation is an amino acid sequence of SEQ ID NO:5.

Preferably, the protein has improved chemical stability in an alkaline condition compared to a protein having an amino acid sequence before introduction of the mutation.

Preferably, the amino acid sequence after introduction of the mutation is any of amino acid sequences of SEQ ID NOs:6 to 18.

The present invention also relates to a multi-domain protein, wherein two or more of the above proteins are connected together.

The present invention also relates to a multi-domain protein, wherein two or more different proteins selected from the above proteins are connected together.

Preferably, the number of the domains of the protein is 2 to 5.

Further, the present invention relates to a DNA encoding the protein or the multi-domain protein.

Preferably, base sequences encoding the connected domains in the DNA have 90% or lower sequence identity to one another.

Further, the present invention relates to a vector including the DNA.

Further, the present invention relates to a transformant obtainable by transformation of a host with the vector.

Preferably, the host is a gram-positive bacterium.

Preferably, the gram-positive bacterium is a bacterium of *Brevibacillus*.

Preferably, the bacterium of *Brevibacillus* is *Brevibacillus choshinensis*.

Further, the present invention relates to a method for producing the protein or the multi-domain protein, the method including utilizing the transformant or a cell-free protein synthesis system using the DNA.

Preferably, the production method includes: accumulating the protein intracellularly and/or in a periplasmic space of the transformant; and/or extracellularly secreting the protein from the transformant.

Further, the present invention relates to an affinity separation matrix, including the protein or the multi-domain protein as an affinity ligand, wherein the protein is immobilized on a carrier made of a water-insoluble base material.

Preferably, the affinity separation matrix binds to a protein containing an Fc region of an immunoglobulin.

Preferably, the protein containing an Fc region of an immunoglobulin is an antibody, antibody derivative, antibody fragment, or antibody fragment derivative.

Preferably, the antibody, antibody derivative, antibody fragment, or antibody fragment derivative is an IgG or an IgG derivative.

Further, the present invention relates to use of the affinity separation matrix for separation of a protein containing an Fc region of an immunoglobulin.

The protein of the present invention has higher alkali resistance than conventional engineered Protein A ligands and has satisfactory antibody dissociation properties in the presence of an acid. Accordingly, the present invention leads to creation of a novel engineered Protein A ligand. Use of an affinity separation matrix in which an engineered Protein A ligand containing the protein is immobilized on a carrier enables separation and purification of an antibody-like molecule, more specifically, an antibody, antibody derivative, antibody fragment, or antibody fragment derivative containing an Fc region of an immunoglobulin.

The E, D, A, B and C domains derived from Protein A have amino acid sequences with high sequence identity to one another. The Gly residues are conserved between these domains, and replacement of the Gly residue in any of these E, D, A, B and C domains with an amino acid other than Ala produces the above effect.

BRIEF DESCRIPTION OF THE DRAWINGS

FIG. 1 is a table for comparison of the sequences of E, D, A, B and C domains of Protein A of Staphylococcus sp. ("_" indicates the same amino acid residue as the corresponding amino acid residue of the C domain), where domains E, D, A, B and C respectively correspond to SEQ ID NOs: 1 to 5 in the sequence listing.

FIG. 5 is a DNA sequence alignment of the DNA sequences of the connected domains which were obtained by reverse translation from the amino acid sequences of five connected C-G29Vs of Example 12 of the present invention. Where the connected domains constitute the nucleotide sequence of SEQ ID No: 58 as is shown in Example 12; the 1st domain is 3 to 176 nucleotides. the 2nd domain is 177 to 370 nucleotides, the 3rd domain is 371 to 524 nuoleotides, the 4th domain is 525 to 698 nucleotides and the 5th domain is 699 to 872 nucleotides.

FIG. 6 shows SDS-PAGE analysis results of (A) a supernatant of a culture of a recombinant bacterium capable of expressing five connected C-G29Vs of Example 13 of the present invention and (B) a supernatant of a culture of a recombinant bacterium capable of expressing five connected C-wilds of Comparative Example 2.

FIG. 7 shows agarose gel electrophoresis results of (A) a plasmid contained in a recombinant bacterium capable of expressing five connected C-G29Vs of Example 13 of the present invention and (B) a plasmid contained in a recombinant bacterium capable of expressing five connected C-wilds of Comparative Example 2.

BEST MODE FOR CARRYING OUT THE INVENTION

Figure 2:
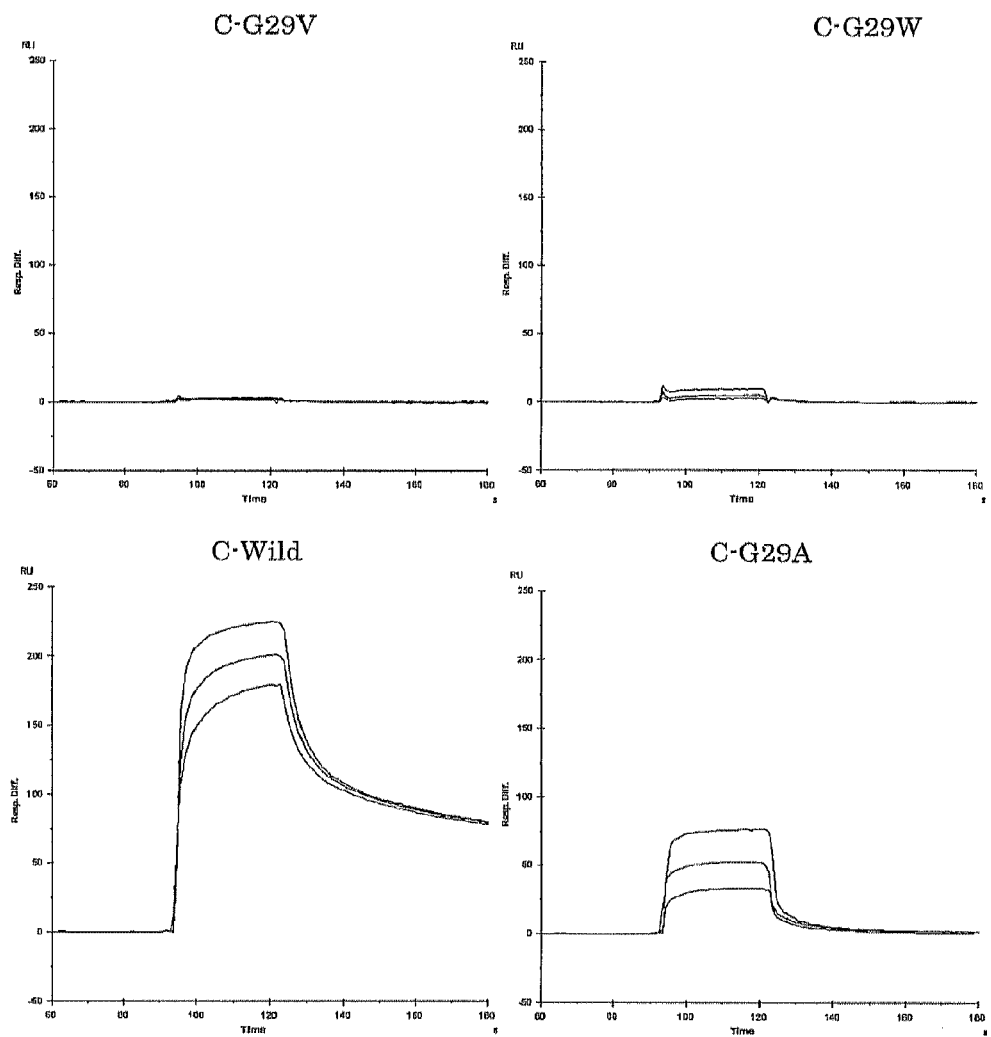
FIG. 2 is sensorgrams of the binding reactions of C-G29V, C-G29W, C-wild and C-G29A of Example 9 of the present invention and Comparative Example 1, with a monoclonal IgG-Fab.

The protein of the present invention has an affinity for an immunoglobulin, and includes an amino acid sequence derived from any of E, D, A, B and C domains of Protein A of SEQ ID NOs:1 to 5. At least one Gly residue in the amino acid sequence is replaced with an amino acid other than Ala. The protein has a lower affinity for an Fab region of an immunoglobulin than a protein including an amino acid sequence in which the Gly residue is replaced with Ala.

Protein A is a protein containing five connected immunoglobulin-binding domains. Several types of microorganisms express Protein A and examples of microorganisms that express Protein A include bacteria of Staphylococcus. The E, D, A, B and C domains of Protein A of SEQ ID NOs:1 to 5 are immunoglobulin-binding proteins capable of binding to a region other than complementarity determining regions (CDRs) of immunoglobulins. All the domains are capable of binding to any region of Fc and Fab regions of immunoglobulins and particularly an Fv region in the Fab region. As shown in the sequence comparison table of FIG. 1, the E, D, A, B and C domains derived from Protein A have amino acid sequences with high sequence identity to one another. The amino acid sequence corresponding to the Gly residue at position 29 and even the amino acid residues at positions 26 to 39 of the C domain is commonly conserved in all of these domains.

The term "an amino acid sequence derived from a domain" means the amino acid sequence before introduction of the mutation and refers to, for example, but not limited to, the wild-type amino acid sequence of any of the E, D, A, B and C domains of Protein A. This term is intended to further include altered amino acid sequences in which partial replacement, insertion, deletion and chemical modification of an amino acid residue are introduced, except for the replacement of the Gly residue corresponding to position 29 of the C domain with an amino acid other than Ala, provided that these amino acid sequences encode proteins having a binding ability to the Fc region. For example, the Z domain produced by introducing the mutations A1V and G29A into the B domain corresponds to a sequence derived from the B domain, and a protein produced by introducing an amino acid residue other than Gly for the Ala residue at position 29 of the Z domain is also included in the protein of the present invention.

The term "protein" herein is intended to include any molecules of polypeptide structure and include fragmentized polypeptide chains and polypeptide chains connected by a peptide bond. The term "domain" means a higher-order protein structural unit consisting of several tens or hundreds of amino acid residues, which is able to fulfill a certain physicochemical or biochemical function.

Replacement of an amino acid residue is represented by the amino acid residue of the wild-type or non-mutated type, the position of the replacement and an amino acid residue introduced by the mutation, in this order. For example, replacement of a Gly residue at position 29 with Ala is represented by G29A.

The number of Gly residues replaced with amino acids other than Ala is not particularly limited, provided that the resulting protein has a lower affinity for the Fab region of an immunoglobulin than a protein having an amino acid sequence in which the residues are replaced with Ala, and has an affinity for an immunoglobulin.

The protein before introduction of the mutation preferably has 85% or higher, and more preferably 90% or higher sequence identity to the wild-type amino acid sequence of any of E, D, A, B and C domains of Protein A, and has a binding ability to the Fc region.

The Gly residue(s) replaced with amino acid(s) other than Ala is/are not particularly limited, provided that it/they is/are in any of the E, D, A, B and C domains of Protein A of SEQ ID NOs:1 to 5. Examples thereof include Gly residues conserved between these domains, and specifically include Gly residues corresponding to position 29 of the C domain. Here, the term "corresponding" means amino acid residues arranged in the same vertical line when the E, D, A, B and C domains of Protein A are aligned as shown in FIG. 1.

Examples of the Gly residues corresponding to position 29 of the C domain include the Gly residue at position 27 of the E domain, the Gly residue at position 32 of the D domain, the Gly residue at position 29 of the A domain and the Gly residue at position 29 of the B domain. Although the positions of these Gly residues in the amino acid sequences may change if insertion, deletion and/or addition of an amino acid residue is/are introduced on the N-terminal side, those skilled in the art can find the target amino acids for the mutation according to the present invention based on amino acid sequences conserved on the both sides of the Gly residues.

Replacement of an amino acid residue refers to a mutation in which the original amino acid residue is deleted and another amino acid is introduced at the same position. The other amino acid(s) to be introduced is/are not particularly limited and examples thereof include natural proteinogenic amino acids, non-proteinogenic amino acids, and non-natural amino acids. In terms of genetic engineering production, natural amino acids are suitably used among these.

The amino acid(s) other than Ala, which is/are introduced by the replacement, is/are not particularly limited but is/are preferably Val, Leu, Ile, Phe, Tyr, Trp, Thr, Asp, Glu, Arg, His, Lys, Met, Cys, Asn and/or Gln. Val, Leu, Ile, Phe, Tyr, Trp, Thr, Asp, Glu, Arg, His and/or Met is/are more preferable among these. For improvement of the chemical stability in an alkaline condition, the amino acid(s) other than Ala introduced by the replacement is/are further preferably Leu, Ile, Phe, Tyr, Trp, Glu, Arg and/or Met, and particularly preferably Phe, Tyr, Trp and/or Met.

Examples of the protein in which a Gly residue is replaced with an amino acid other than Ala as described above include a protein having an amino acid sequence derived from the C domain of Protein A of SEQ ID NO: 5, in which the Gly residue at position 29 is replaced with an amino acid other than Ala.

If the protein of the present invention has this amino acid replacement mutation, the chemical stability in an alkaline condition is improved compared to proteins in which the Gly residue is replaced with Ala. In particular, a protein produced by introducing this mutation into the amino acid sequence of the C domain has higher chemical stability in an alkaline condition than proteins derived from the other E, D, A and B domains.

In the case where a protein pharmaceutical is purified through a column for chromatographic purification such as an affinity column, an alkaline solution is optionally used for example for the purpose of washing remaining substances, such as organic matter, off from the column. The term "in an alkaline condition" used herein means an alkalinity that makes it possible to achieve the purpose of washing. More specifically, the term corresponds to, but is not limited to, an about 0.05 to 1.0 N sodium hydroxide aqueous solution, for example.

The term "chemical stability" herein refers to the resistance of the protein to chemical modification such as a chemical change of an amino acid residue and chemical denaturation such as transition or cleavage of an amide linkage, and the ability of the protein to maintain its function. The "ability of the protein to maintain its function" herein refers to binding activity to the Fc region of an immunoglobulin (the proportion of the protein resistant to chemical denaturation and capable of maintaining the affinity). A higher level of the "chemical stability" corresponds to a smaller reduction of the binding ability to the Fc region of an immunoglobulin through immersion in an alkaline solution.

For example, in the case where two proteins, a wild-type protein and a protein after mutagenesis, at the same molar concentration are treated for 25 hours at 30° C. in a 0.5 N sodium hydroxide solution, if the remaining affinities for the Fc region of an immunoglobulin of the treated wild-type protein and protein after mutagenesis are 40% and 50% of the binding activities of these proteins at the same molar concentration before the treatment, respectively, the protein after mutagenesis is considered to be more stable in an alkaline condition than the wild-type protein. The "chemical stability" used herein is considered to be improved in the case where the remaining binding activity of the protein after mutagenesis after immersion into an alkaline solution that reduces the binding activity of the wild-type protein to 10 to 40% is 5% or more higher, preferably 10% or more higher, and more preferably 15% or more higher than the remaining binding activity of the wild-type protein after the same treatment. The term "alkali resistance" herein is synonymous with the "chemical stability in an alkaline condition".

The protein produced by introducing the replacement mutation preferably has 85% or higher, and more preferably 90% or higher sequence identity to the wild-type amino acid sequence of any of E, D, A, B and C domains of Protein A.

Specific examples of the protein include proteins having the amino acid sequences of SEQ ID NOs:6 to 18.

The protein of the present invention may be a protein consisting of a single domain, and may be a multimer protein (a multi-domain protein) in which two or more, more preferably 2 to 10, and further more preferably 2 to 5 monomer proteins or domains are preferably connected together. Such a multimer protein may be a homopolymer, such as homodimer and homotrimer, in which the same immunoglobulin-binding domains are connected together, or a heteropolymer, such as heterodimer and heterotrimer, in which different immunoglobulin-binding domains are connected together.

One example of the connection between monomer proteins in the present invention is a connection by one or more amino acid residues. However, the connection is not limited to this, and the number of amino acid residues involved in the connection is not particularly limited. Preferably, the connection does not destabilize the three-dimensional conformation of the monomer proteins.

The protein or the multi-domain protein of the present invention may be available in the form of a fusion protein with a protein that is known to beneficially facilitate expression or purification of a protein. Examples of such fusion proteins include, but are not limited to, a fusion protein with albumin, MBP (maltose-binding protein) or GST (glutathione S-transferase). Fusion proteins with a nucleic acid (e.g. DNA aptamer), a drug (e.g. antibiotic substance) or a polymer (e.g. PEG (polyethylene glycol)) are also intended to be included in the scope of the present invention, provided that these fusion proteins make use of the advantages of the protein of the present invention.

The present invention also relates to a DNA having a base sequence encoding the protein obtained by the method described above. The DNA may be any DNA, provided that the amino acid sequence produced from translation of the base sequence of the DNA constitutes the protein. Such a DNA can be obtained by common known techniques, for example, using polymerase chain reaction (hereinafter, abbreviated as PCR) technology. Alternatively, such a DNA can be synthesized by known chemical synthesis techniques or is available from DNA libraries. A codon in the base sequence of the DNA may be replaced with a degenerate codon, and the base sequence is not necessarily the same as the original base sequence, provided that the translated amino acids are the same as those encoded by the original base sequence.

Site-directed mutagenesis of the DNA encoding the protein of the present invention can be carried out as follows, using recombinant DNA technology, PCR technology or the like.

In the case of mutagenesis by recombinant DNA technology, for example, if there are suitable restriction enzyme recognition sequences on both sides of a mutagenesis target site in the gene encoding the protein of the present invention, cassette mutagenesis can be used in which a region containing the mutagenesis target site is removed by cleaving these restriction enzyme recognition sites with the restriction enzymes and a mutated DNA fragment is inserted only into the target site by a method such as chemical synthesis.

In the case of site-directed mutagenesis by PCR, for example, double primer mutagenesis can be used in which PCR is carried out using a double-stranded plasmid encoding the protein as a template, and two kinds of synthesized oligo primers which contain complementary mutations in the + and − strands.

A DNA encoding a multimer protein can be produced by ligating the desired number of DNAs each encoding a monomer protein (single domain) of the present invention to one another in tandem. For example, ligation to produce such a DNA encoding a multimer protein can be accomplished by introducing a suitable restriction enzyme site into the DNA sequences, and ligating double-stranded DNA fragments cleaved with the restriction enzyme using a DNA ligase. Only one restriction enzyme recognition site may be introduced or restriction enzyme sites of different types may be introduced.

Production of such a DNA encoding a multimer protein is not limited to these ligation processes, and may be accomplished, for example, by performing the aforementioned mutagenesis technologies on a DNA encoding Protein A (for example, WO 06/004067). If the base sequences encoding monomer proteins in the DNA encoding the multimer protein are the same, homologous recombination may be induced in a host. Thus, the ligated DNAs encoding monomer proteins preferably have 90% or lower base sequence identity and more preferably 85% or lower base sequence identity to one another.

The vector includes a DNA encoding the whole or a part of the amino acid sequence of the protein and a promoter that is operably linked to the base sequence to function in a host. Typically, the vector can be constructed by linking or inserting a DNA including a gene encoding the protein to a suitable vector. The vector for insertion of the gene is not particularly limited, provided that it is capable of autonomous replication in a host. As such a vector, a plasmid DNA or phage DNA can be used. For example, in the case of using *Escherichia coli* as a host, a pQE series vector (QIAGEN), a pET series vector (Merck), a pGEX series vector (GE health care, Japan) or the like vector can be used.

In the case of using a bacterium of *Brevibacillus* as a host to be transformed, examples of the vector include the known *Bacillus subtilis* vector pUB110, and pHY500 (JP H2-31682 A), pNY700 (JP H4-278091 A), pNU211R2L5 (JP H7-170984 A), and pHT210 (JP H6-133782 A), and the shuttle vector pNCMO2 between *Escherichia coli* and *Brevibacillus* sp. (JP 2002-238569 A)

A transformant can be produced by introducing the vector of the present invention into a host cell. Transformation of a host with the vector can be accomplished by, for example, but not limited to, using calcium ions, electroporation, spheroplast transformation, lithium acetate transformation, *agrobacterium* infection, particle gun transformation or a polyethylene-glycol method. The vector can be maintained in a host, for example, by autonomous replication of the vector in the cell independently of genome (chromosome) replication. Alternatively, the produced gene may be integrated into the genome (chromosome) and maintained by replication accompanying the genome replication.

The host cell is not particularly limited. Preferred examples of those suited for low-cost mass production include *Escherichia coli*, *Bacillus subtilis* and bacteria of genera including *Brevibacillus*, *Staphylococcus*, *Streptococcus*, *Streptomyces*, and *Corynebacterium* (eubacteria). More preferred are gram-positive bacteria such as *Bacillus subtilis* and bacteria of genera including *Brevibacillus*, *Staphylococcus*, *Streptococcus*, *Streptomyces*, and *Corynebacterium*. Still more preferred are bacteria of *Breviacillus*, which are known to be used for mass production of Protein A (WO 06/004067).

The bacteria of *Brevibacillus* are not particularly limited and examples thereof include *Brevibacillus agri*, *B. borstelensis*, *B. brevis*, *B. centrosporus*, *B. choshinensis*, *B. formosus*, *B. invocatus*, *B. laterosporus*, *B. limnophilus*, *B. parabrevis*, *B. reuszeri*, and *B. thermoruber*. Preferred examples thereof include *Brevibacillus brevis* 47 (JCM6285), *Brevibacillus brevis* 47K (FERN BP-2308), *Brevibacillus brevis* 47-5Q (JCM8970), *Brevibacillus choshinensis* HPD31 (FERN BP-1087) and *Brevibacillus choshinensis* HPD31-OK (FERN BP-4573). Mutant strains (or derivative strains) such as protease-deficient strains, high-expression strains or sporulation-deficient strains of the bacteria of *Brevibacillus* may be used according to purposes such as improvement in yields. Specifically, the protease mutant strain HPD31-OK of *Brevibacillus choshinensis* (JP H6-296485 A) and the sporulation-deficient strain HPD31-SP3 of *Brevibacillus choshinensis* (WO 05/045005) derived from *Brevibacillus choshinensis* HPD31 can be used.

The protein of the present invention can be produced using a transformant or a cell-free protein synthesis system using the DNA.

In the case of using a transformant for the production of the protein, the protein can be accumulated in the transformant cell (including the periplasmic space) or extracellularly accumulated in the culture solution, and recovered therefrom. In the case where the expressed protein is accumulated in the cell, the protein can be protected from oxidation. Another advantage of this case is that side reactions with medium components can be avoided. In the case where the expressed protein is accumulated in the periplasmic space, decomposition by an intracellular protease can be advantageously inhibited. In the case where the protein is extracellularly secreted from the transformant, advantageously, processes for disrupting and extracting the cells are not required, resulting in reduced production costs.

Specifically, in the case where the protein is accumulated in the cultured cells (including the periplasmic space), the protein accumulated in the cells can be recovered, for example, by collecting the cells from the culture solution by centrifugation, filtration or the like, and then disrupting the cells by sonication, a French press treatment or the like, and/or solubilizing the protein by adding a surfactant or the like. In the case where a recombinant protein is secreted, the produced recombinant protein can be recovered after the culture period by separating the cultured cells and the supernatant containing the secreted protein by common separation methods such as centrifugation and filtration.

In the case where the protein of the present invention is produced by a cell-free protein synthesis system, the cell-free protein synthesis system is not particularly limited, provided that the system is capable of synthesizing the protein in vitro using a cell extract. Examples thereof include synthesis systems derived from procaryotes, plant cells, or higher animal cells.

The protein of the present invention can also be produced by culturing the transformant in a medium; allowing the transformant to express the protein in the form of a fusion protein with another protein; collecting the fusion protein from the culture; cleaving the fusion protein with a suitable protease; and collecting the desired protein.

The transformant of the present invention can be cultured in a medium in accordance with a common method for culturing host cells. The medium used for culturing the produced transformant is not particularly limited, provided that it enables high yield production of the protein at high efficiency. Specifically, carbon and nitrogen sources such as glucose, sucrose, glycerol, polypeptone, meat extracts, yeast extracts, and casamino acids can be used. In addition, the medium is supplemented, as required, with inorganic salts such as potassium salts, sodium salts, phosphates, magnesium salts, manganese salts, zinc salts, and iron salts. In the case of an auxotrophic host cell, nutritional substances necessary for its growth may be added to the medium. Moreover, antibiotics such as penicillin, erythromycin, chloramphenicol, and neomycin may optionally be added.

In the case of a transformant produced from an *Escherichia coli* host, the medium for culturing the transformant is not particularly limited and examples thereof include LB medium (triptone 1%, yeast extract 0.5%, NaCl 1%) and 2xYT medium (triptone 1.6%, yeast extract 1.0%, NaCl 0.5%).

In the case of a transformant produced from a *Brevibacillus* host, the medium for culturing the transformant is not particularly limited and examples thereof include TM medium (peptone 1%, meat extract 0.5%, yeast extract 0.2%, glucose 1%, pH 7.0) and 2SL medium (peptone 4%, yeast extract 0.5%, glucose 2%, pH 7.2).

Furthermore, a variety of known protease inhibitors, phenylmethane sulfonyl fluoride (PMSF), benzamidine, 4-(2-aminoethyl)-benzenesulfonyl fluoride (AEBSF), antipain, chymostatin, leupeptin, pepstatin A, phosphoramidon, aprotinin, and ethylenediaminetetra acetic acid (EDTA), and/or other commercially available protease inhibitors may be added at appropriate concentrations in order to inhibit the degradation or molecular-size reduction of the target protein caused by a host-derived protease present inside or outside the bacterial cells.

In order to assist accurate folding of the protein of the present invention, a molecular chaperone such as GroEL/ES, Hsp70/DnaK, Hsp90 and Hsp104/C1pB may be used. For example, such a molecular chaperone is coexpressed with the protein of the present invention or is allowed to coexist with the protein of the present invention by combination into a fusion protein or the like. Other examples of techniques for accurate folding of the protein include, but are not limited to, addition of an additive for assisting accurate folding into the medium; and culturing at a low temperature.

The protein can be produced by aerobic culture at a temperature of 15° C. to 42° C., preferably 20° C. to 37° C., for several hours to several days in an aeration-stirring condition. In some cases, the culture may be performed anaerobically without aeration.

Purification of the protein can be accomplished by any one or an appropriate combination of techniques such as affinity chromatography, cation or anion exchange chromatography and gel filtration chromatography.

Examples of techniques to confirm whether the obtained purified product is a target protein include common techniques such as SDS polyacrylamide gel electrophoresis, N-terminal amino acid sequence analysis and Western blot analysis.

An affinity separation matrix can be obtained by immobilizing as an affinity ligand the protein of the present invention on a carrier made of a water-insoluble base material. The term "affinity ligand" refers to a substance (functional group) that selectively captures (binds to) a target molecule from a mixture of molecules based on specific affinity between molecules such as an antigen and antibody binding, and refers herein to a protein that specifically binds to an immunoglobulin. The term "ligand" as used alone herein is synonymous with an "affinity ligand".

Examples of the carrier made of a water-insoluble base material used in the present invention include inorganic carriers such as glass beads and silica gel; organic carriers such as synthetic polymers (e.g. cross-linked polyvinyl alcohol, cross-linked polyacrylate, cross-linked polyacrylamide, cross-linked polystyrene) and polysaccharides (e.g. crystalline cellulose, cross-linked cellulose, cross-linked agarose, cross-linked dextran); and composite carriers of combinations of these carriers such as organic-organic or organic-inorganic composite carriers. Examples of commercial products thereof include GCL2000 (porous cellulose gel available from Seikagaku Corp.), Sephacryl S-1000 (covalently cross-linked copolymer of allyl dextran and methylene bis acrylamide available from GE health care, Japan), Toyopearl (acrylate carrier available from Tosoh Corp.), Sepharose CL4B (cross-linked agarose carrier available from GE health care, Japan) and Cellufine (cross-linked cellulose carrier available from Chisso Corp.). It should be noted that the water-insoluble carrier usable in the present invention is not limited to the carriers listed above.

In view of the purpose and method of usage of the affinity separation matrix, the water-insoluble carrier used in the present invention preferably has a larger surface area and is preferably a porous matrix having a large number of fine pores with a suitable size. The carrier may be in any form such as bead, monolith, fiber, or film (including hollow fiber).

Immobilization of the ligand on the carrier may be accomplished, for example, by a conventional coupling method utilizing an amino, carboxyl or thiol group of the ligand. Examples of such a coupling method include an immobilization method including activation of a carrier by the reaction with cyanogen bromide, epichlorohydrin, diglycidyl ether, tosyl chloride, tresyl chloride, hydrazine, sodium periodate, or the like (or introduction of a reactive functional group into the carrier surface), and the coupling reaction between the resulting carrier and a compound to be immobilized as a ligand; and an immobilization method involving condensation and crosslinking which includes adding a condensation reagent such as carbodiimide or a reagent having a plurality of functional groups in the molecule, such as glutaraldehyde, into a system containing a carrier and a compound to be immobilized as a ligand.

A spacer molecule consisting of a plurality of atoms may be introduced between the ligand and the carrier, or alternatively, the ligand may be directly immobilized on the carrier. Accordingly, for immobilization, the protein of the present invention may be chemically modified, or may include an additional amino acid residue useful for immobilization.

Examples of amino acids useful for immobilization include amino acids having a functional group useful for a chemical reaction for immobilization in a side chain, and specifically include Lys which includes an amino group in a side chain, and Cys which includes a thiol group in a side chain. Even if the protein of the present invention is modified or altered in any manner for immobilization, the matrix including as a ligand the protein of the present invention immobilized therein is included within the scope of the present invention, provided that the matrix still maintains the effect of the protein of the present invention.

Preferably, the affinity separation matrix binds to a protein containing the Fc region of an immunoglobulin. Examples of the protein containing the Fc region of an immunoglobulin to which the affinity separation matrix binds include antibodies, antibody derivatives, antibody fragments, and antibody fragment derivatives containing the Fc region of an immunoglobulin. These proteins can be separated and purified by affinity column chromatography purification.

Examples of the "antibodies containing the Fc region of an immunoglobulin" include IgG. In this case, the term "antibody derivatives" refers to IgG derivatives and specific examples thereof include chimeric antibodies in which domain (s) of a human IgG is/are partially replaced and fused with IgG domain(s) of another species, and humanized antibodies in which CDRs of a human IgG are replaced and fused with antibody CDRs of another species. Examples of the "antibody fragments" include a protein consisting of the Fc region of a human IgG. Examples of the "antibody fragment derivatives" include an artificial antibody in which the Fv region and the Fc region of a human IgG are fused. The term "antibody-like molecule" is used herein as a generic term to refer to these antibodies, antibody derivatives, antibody fragments and antibody fragment derivatives.

The use of the affinity separation matrix enables separation of proteins containing the Fc region of an immunoglobulin. Separation of proteins containing the Fc region (e.g. antibodies, antibody derivatives, antibody fragments and antibody fragment derivatives mentioned above) can be accomplished by procedure in accordance with affinity column chromatography purification using an already commercially available Protein A column (Non-Patent Document 3). Specifically, the pH of a buffer containing an antibody, antibody derivative, antibody fragment, or antibody fragment derivative is adjusted to neutral, and the solution is allowed to pass through an affinity column filled with the affinity separation matrix of the present invention, so that the antibody, antibody derivative, antibody fragment, or antibody fragment derivative is adsorbed. Next, the inside of the affinity column is washed by running an adequate amount of a pure buffer through the column. At this point, the target antibody, antibody derivative, antibody fragment, or antibody fragment derivative is still adsorbed on the affinity separation matrix of the present invention in the column. Next, an acid buffer (optionally containing a substance for promoting dissociation from the matrix) with a pH appropriately adjusted is allowed to pass through the column, so that the target antibody, antibody derivative, antibody fragment, or antibody fragment derivative is eluted. Higher purity can be achieved by this purification procedure.

Reuse of the affinity separation matrix of the present invention is enabled by washing the matrix by running an adequate strong acid or strong alkali pure buffer which does not completely impair the functions of the ligand compound and the base material of the carrier (or optionally a solution containing an adequate modifying agent or an organic solvent), through the column.

Generally, the domains of Protein A more strongly bind to the Fc region than to the Fab region (Non-Patent Document 3). Thus, the term "affinity for an immunoglobulin" of the protein of the present invention essentially refers to the affinity for the Fc region, and the level of the affinity for an immunoglobulin does not largely change even if only the binding strength to the Fab region is changed. The protein of the present invention is lower in the secondary affinity for the Fab region, which is derived from the immunoglobulin-binding domains of Protein A. Therefore, the protein of the present invention produces an effect of avoiding an influence of the secondary binding in the interaction with the immunoglobulin. However, the affinity for an immunoglobulin as a whole is maintained because the affinity for the Fc region is maintained. In the case where the affinity of the protein of the present invention for an immunoglobulin is evaluated as an affinity for a human immunoglobulin G drug using a Biacore system described below, the affinity constant (KA) is preferably $10^6$ (M$^{-1}$) or higher, and is more preferably $10^7$ (M$^{-1}$) or higher.

The affinity of the protein of the present invention for an immunoglobulin can be measured by, for example, a biosensor such as a Biacore system using the surface plasmon resonance principle (GE health care, Japan). However, the measuring method is not limited to this.

The measurement condition may be appropriately determined so that a binding signal of Protein A binding to the Fc region of an immunoglobulin can be detected. Specifically, the affinity can be easily evaluated at a temperature of 20° C. to 40° C. (constant temperature) and a neutral pH of 6 to 8.

Examples of targets for which the protein of the present invention has an affinity include, but are not limited to, immunoglobulin molecules containing the whole Fab and Fc regions, and derivatives thereof. Since the protein of the present invention has an affinity for a protein containing a part of the Fc region, the binding target is not necessarily a protein containing the whole Fc region. Since the conformation of the antibodies is known, it is possible to further alter (e.g. fragmentation) the Fab or Fc region by a protein engineering technique while maintaining the conformation of the region to which the protein of the present invention binds. The protein of the present invention is capable of binding to such derivatives. Examples of the protein of the present invention include a protein having an affinity for the Fc region of an IgG of the subtype 1, 2 or 4, which has a lower affinity for the Fab region of an IgG of the VH3 subfamily than a protein in which the Gly residue at position 29 of the C domain is replaced with Ala.

The immunoglobulin molecule as a binding partner used for the measurement of the affinity for the Fab region of an immunoglobulin is not particularly limited, provided that it allows detection of binding to the Fab region. However, Fab fragments or Fv fragments obtained by fragmentizing immunoglobulin molecules so as to remove the Fc region are preferable because binding to the Fc region is also detected in the case of an immunoglobulin molecule containing the Fc region.

It is possible to confirm whether the protein of the present invention is binding to the Fab region of an immunoglobulin by using a human IgG of the VH3 subfamily (a monoclonal antibody). More preferred is an Fab fragment of an immunoglobulin of the VH3 subfamily, which is known to have an Fab region to which Protein A binds. Nearly half of human VH germline genes belong to the VH3 subfamily, and in fact, pharmaceuticals containing IgG antibodies of the VH3 subfamily are under study and some of them are already commercially available. In addition, it is regarded as a known fact that the remaining binding ability to the Fab region of an immunoglobulin of the VH3 subfamily produces a bad effect on the antibody dissociation properties in the presence of an acid, from literatures (Ghose S. et al., Biotechnology and bioengineering, 2005, vol. 92, No. 6)

The difference in affinity can be easily analyzed by those skilled in the art, specifically by obtaining sensorgrams of the binding reactions with the same immunoglobulin molecule in the same measurement condition, and making a comparison with a binding parameter obtained by analyzing the data of a protein in which the Gly residue corresponding to position 29 of the C domain is replaced with Ala. Here, the sequences to be compared for the difference in affinity should be the same except for the mutation position (position 29 in the case of the C domain). For example, in the case where the comparison target is a B-domain mutant in which the Gly residue at position 29 is replaced with Ala, a B-domain mutant in which the Gly residue at position 29 is replaced with an amino acid other than Ala is appropriate for the comparison, and a C-domain mutant in which the Gly residue at position 29 is replaced with an amino acid other than Ala, for example, is inappropriate for the comparison.

Examples of binding parameters include the affinity constant (KA) and the dissociation constant (KD) (Nagata et al., "Real-time analysis of biomolecular interactions", Springer-Verlag Tokyo, 1998, page 41). The affinity constant between the domain mutants according to the present invention and the Fab can be determined, for example, by using a Biacore system and adding each domain mutant to a flow channel in an experimental system in which an Fab fragment of an immunoglobulin of the VH3 subfamily is immobilized on a sensor chip, at 25° C. at a pH of 7.4. A suitable mutant in which the Gly residue at position 29 is replaced with an amino acid other than Ala is one preferably having an affinity constant (KA) of not higher than ½, more preferably not higher than ⅕, and further more preferably not higher than 1/10 of the affinity of a corresponding mutant in which the Gly residue at position 29 is replaced with Ala. Specifically, a C-domain mutant in which the Gly residue at position 29 is replaced with Ala generally has a KA to the Fab of $1\times10^4$ to $1\times10^5$ $(M^{-1})$, and a mutant suitably used in the present invention is a C-domain mutant in which the Gly residue at position 29 is replaced with an amino acid other than Ala and whose KA is $1\times10^4$ $(M^{-1})$ or lower. More suited is a mutant whose KA is $0.5\times10^4$ $(M^{-1})$ or lower. Examples of the Fab usable in the KA measurement include an Fab obtained by fragmentizing an immunoglobulin G into an Fab fragment and Fc fragment with papain; and an Fab produced using a production system that is produced by a genetic engineering technique to express only the Fab region of an immunoglobulin G.

The binding activity to an immunoglobulin after a chemical treatment can be analyzed by, but not limited to, using a biosensor such as a Biacore system using the surface plasmon resonance principle (GE health care, Japan) in the same manner as described above. However, for the binding activity after a chemical treatment (for a comparison with that before the chemical treatment), the affinity constant (KA) and dissociation constant (KD) are inappropriate as binding parameters (because the binding ability of a protein molecule to an immunoglobulin is not changed by a chemical treatment). The remaining binding activity of the protein after a chemical treatment is preferably determined, for example, by immobilizing the protein on a sensor chip, and determining as a binding parameter the magnitude of a binding signal or the theoretical maximum binding capacity (Rmax) at the time of addition of the same concentration of an immunoglobulin, before and after the chemical treatment of the protein. However, the method for determining the remaining binding activity is not limited to this, and the remaining binding activity may be determined by adding the protein before and after a chemical treatment into an experimental system in which an immunoglobulin is immobilized.

Owing to its reduced binding ability to the Fab region of an immunoglobulin as mentioned above, the affinity separation matrix excellently dissociates an antibody in the process of eluting the antibody in an acid solution. Specifically, since the affinity separation matrix allows elution in an acidic elution condition closer to the neutral condition, damage to an antibody in an acidic condition can be advantageously avoided. The acidic elution condition closer to the neutral condition specifically refers to one with a pH closer to the neutral (a pH of about 3.0 to 5.0) than the pH range of a common acidic elution condition of about 2.0 to 3.5. Elution in this condition reduces damage to an antibody (Ghose S. et al., Biotechnology and bioengineering, 2005, vol. 92, No. 6). The "excellent antibody dissociation properties in the presence of an acid" means, for example, dissociation in an acidic elution condition closer to the neutral condition, or a sharper elution peak profile obtained when an antibody is eluted in an acidic elution condition. A sharper elution peak profile of chromatography indicates that a higher concentration and smaller amount of antibody-containing eluate is recovered.

Further, the present invention provides the matrix which is excellent in dissociating an antibody in an acid solution and has high chemical stability in an alkaline condition. Specifically, the present invention provides a matrix that can reduce damage to ligand molecules in the process of washing with a sodium hydroxide aqueous solution (about 0.05 M to 1 M) for removing impurities (such as proteins derived from a host, carbohydrates, lipids, bacteria and viruses) from the matrix so that the matrix can be reused. Here, the washing process required for reuse of the matrix is not limited to the washing process using a sodium hydroxide aqueous solution, but this process can be implemented at lower cost and provide a high washing and bactericidal effect.

EXAMPLES

The present invention is described in more detail below based on Examples, but is not limited to these Examples. Proteins (single-domain proteins free from connected domains) produced in Examples may each be represented by "an alphabet indicating the domain—an introduced mutation (Wild for the wild-type)". For example, the wild-type C domain is represented by "C-wild", and a C-domain mutant with the mutation G29V is represented by "C-G29V". Replacement mutations of the Gly residues corresponding to position 29 of the C domain with an amino acid other than Ala in the present invention are generically referred to as "G29Xs", and for example, a mutant of the C domain with this mutation of the present invention is represented by "C-G29X".

Example 1

Preparation of DNA Encoding Wild-type C Domain (C-wild)

A DNA fragment (177 bp) encoding C-wild (SEQ ID NO:5) was amplified by PCR using the oligonucleotide primers of SEQ ID NOs:19 and 20 and the expression vector pNK3262NX encoding wild-type Protein A as a template. The vector pNK3262NX used as a template is a known Protein A expression vector produced by altering a part of the vector pNK3260, and encodes wild-type Protein A except a part of the cell wall-anchoring domain X and the like (WO 06/004067). The base sequence encoding the C-wild produced in the present example is shown as SEQ ID NO:21. The oligonucleotide primers of SEQ ID NOs:19 and 20 were constructed such that DNAs amplified using these primers had restriction enzyme recognition sites BamHI and EcoRI on the opposite sides of the gene encoding the C-wild and that the C-wild had a Cys residue on the C-terminal side (downstream of Lys-58)

The obtained DNA fragment was digested with the restriction enzymes BamHI and EcoRI (both available from Takara) and the resulting fragments were purified and recovered. The GST fusion protein expression vector pGEX-6P-1 (GE health care, Japan) was digested with the restriction enzymes BamHI and EcoRI and the resulting fragments were purified and recovered. In addition, the recovered fragments were treated with alkaline phosphatase for dephosphorylation. Subsequently, the resulting DNA fragment encoding the C-wild and the resulting expression vector pGEX-6P-1 were ligated to each other with the DNA ligase Ligation High (TOYOBO CO., LTD.). In this manner, a GST fused C-wild expression plasmid was constructed.

*Escherichia coli* HB 101 (Takara) was transformed using the expression plasmid containing the gene encoding the C-wild produced by the above procedure, and the plasmid DNA was amplified and extracted by a common method.

Example 2

Preparation of DNA Encoding Wild-type B Domain (B-wild)

As shown in FIG. 1, the amino acid sequence of B-wild (SEQ ID NO:4) can be obtained by introducing the mutations T23N, V40Q, K42A, E43N and I44L into the C-wild. Therefore, a DNA encoding the B-wild was prepared by introducing the mutations T23N, V40Q, K42A, E43N and I44L into the DNA (SEQ ID NO:21) encoding the C-wild. A plasmid containing a gene encoding an amino acid sequence in which the mutation of T23N was introduced into the C-wild was obtained by quick change mutagenesis using the oligonucleotide primers of SEQ ID NOs:22 and 23 and the C-wild expression plasmid produced in Example 1 as a template. Then, a GST fused B-wild expression plasmid containing a gene encoding the B-wild was produced by introducing the mutations V40Q, K42A, E43N and I44L by quick change mutagenesis in the same manner as described above, using the oligonucleotide primers of SEQ ID NOs:24 and 25 and the produced plasmid as a template.

*Escherichia coli* HB 101 (Takara) was transformed using the expression plasmid, and the plasmid DNA was amplified and extracted by a common method. The DNA sequence encoding the B-wild produced in the present example is shown as SEQ ID NO:26.

The quick change mutagenesis was performed in accordance with the protocol of Stratagene using a Pfu Turbo DNA polymerase and the methylated DNA (template DNA) cleavage enzyme DpnI (both available from Stratagene).

Example 3

Introduction of Mutation at Gly-29

Genes encoding mutants were prepared by quick change mutagenesis using primers of SEQ ID NOs:27 to 52 shown in Table 1, and the C-wild expression plasmid produced in Example 1 and the B-wild expression plasmid produced in Example 2 as templates.

Expression plasmids encoding the C-domain mutants (C-G29Xs) of SEQ ID NOs:6 to 18 in which the Gly-29 in the amino acid sequence of SEQ ID NO:5 was replaced with Val, Leu, Ile, Tyr, Phe, Thr, Trp, Ser, Asp, Glu, Arg, His, or Met, were produced using the C-wild expression plasmid as a template. Likewise, expression plasmids encoding the B-domain mutants (B-G29Xs) of SEQ ID NOs:53 to 56 in which the Gly-29 in the amino acid sequence of SEQ ID NO:4 was replaced with Val, Arg, Asp, or Trp, were produced using the B-wild expression plasmid as a template.

*Escherichia coli* HB 101 cells were transformed using the expression plasmids containing genes encoding SEQ ID NOs:6 to 18 and 53 to 56 produced by the above procedure, and the plasmid DNAs were amplified and extracted by a common method.

Table 1 shows for which mutation each of the primers of SEQ ID NOs:27-52 was used.

TABLE 1

| Mutations | Sequences of synthesized oligonucleotides | SEQ ID NOs |
|---|---|---|
| G29V | CAACGTAACGTGTTCATCCAAAG | 27 |
| | CTTTGGATGAACACGTTACGTTG | 28 |
| G29L | CAACGTAACCTGTTCATCCAAAG | 29 |
| | CTTTGGATGAACAGGTTACGTTG | 30 |
| G29I | CAACGTAACATCTTCATCCAAAG | 31 |
| | CTTTGGATGAAGATGTTACGTTG | 32 |
| G29Y | CAACGTAACTACTTCATCCAAAG | 33 |
| | CTTTGGATGAAGTAGTTACGTTG | 34 |
| G29F | CAACGTAACTTCTTCATCCAAAG | 35 |
| | CTTTGGATGAAGAAGTTACGTTG | 36 |
| G29T | CAACGTAACACCTTCATCCAAAG | 37 |
| | CTTTGGATGAAGGTGTTACGTTG | 38 |
| G29W | CAACGTAACTGGTTCATCCAAAG | 39 |
| | CTTTGGATGAACCAGTTACGTTG | 40 |
| G29S | CAACGTAACAGCTTCATCC | 41 |
| | GGATGAAGCTGTTACGTTG | 42 |
| G29D | CAACGTAACGACTTCATCCAAAG | 43 |
| | CTTTGGATGAAGTCGTTACGTTG | 44 |
| G29E | CAACGTAACGAATTCATCCAAAG | 45 |
| | CTTTGGATGAATTCGTTACGTTG | 46 |
| G29R | CAACGTAACCGCTTCATCCAAAG | 47 |
| | CTTTGGATGAAGCGGTTACGTTG | 48 |
| G29H | CAACGTAACCACTTCATCCAAAG | 49 |
| | CTTTGGATGAAGTAGTTACGTTG | 50 |
| G29M | CAACGTAACATGTTCATCCAAAG | 51 |
| | CTTTGGATGAACATGTTACGTTG | 52 |

Example 4

DNA Sequence Determination

The base sequences of the expression plasmid DNAs encoding the C-wild, C-G29Xs, B-wild and B-G29Xs produced in Examples 1 to 3 were determined using the DNA sequencer 3130xl Genetic Analyzer (Applied Biosystems). Using a BigDye Terminator v. 1.1 Cycle Sequencing Kit (Applied Biosystems) in accordance with the attached protocol, PCR of these plasmid DNAs for sequencing was carried out, and the sequencing products were purified and sequenced.

Example 5

Expression of Target Protein

Each of the transformants produced in Example 3 which were capable of expressing the C-G29Xs and B-G29Xs in the form of GST fusion proteins was cultured in LB medium containing ampicillin at 37° C. overnight. A 5 mL aliquot of each culture was inoculated in 2xYT medium (200 mL, ampicillin included) and cultured at 37° C. for about 1 hour. IPTG (isopropyl-1-thio-β-D-galactoside) was added to a final culture concentration of 0.1 mM, and each transformant was further cultured at 37° C. for 18 hours.

After the culture, cells were collected by centrifugation and resuspended in 5 mL of PBS buffer containing EDTA (0.5 mM). The cells were sonicated and centrifuged to separate a supernatant fraction (cell-free extract) and an insoluble fraction.

When a target gene is introduced into a multiple cloning site of the pGEX-6P-1 vector, a fusion protein with GST attached to the N terminal is expressed. In an SDS electrophoretic analysis, a protein band assumed to be induced by IPTG was detected at a position corresponding to a molecular weight of about 33,000 for all of these cell-free extracts obtained from the transformant cultures.

Example 6

Purification of Target Protein

The GST fusion protein was (partially) purified from each cell-free extract containing the GST fusion protein produced in Example 5 by affinity chromatography using a GSTrap FF column (GE health care, Japan), which has an affinity for GST. Each cell-free extract was applied to the GSTrap FF column and the column was washed with a standard buffer (20 mM $NaH_2PO_4$—$Na_2HPO_4$, 150 mM NaCl, pH 7.4). Then, the target GST fusion protein was eluted using an elution buffer (50 mM Tris-HCl, 20 mM Glutathione, pH 8.0).

When a gene is introduced into a multiple cloning site of the pGEX-6P-1 vector, an amino acid sequence that allows cleavage of GST with PreScission Protease (GE health care, Japan) is introduced between GST and a target protein. PreScission Protease was added to each GST fusion protein (PreScission Protease was added in an amount of 2 Units per mg of each GST fusion protein) and the resulting mixture was incubated for 16 hours at 4° C.

After the GST cleavage reaction, each target protein was separated from the reaction solution containing the target protein by gel filtration chromatography using a Superdex 75 10/300 GL column (GE health care, Japan). Specifically, each reaction solution was applied into the Superdex 75 10/300 GL column equilibrated with a standard buffer, and the target protein therein was separated and purified from the cleaved GST and PreScission Protease.

A band assumed to be each target protein was detected at a position corresponding to a molecular weight of about 6,800 by a tricine-SDS electrophoretic analysis of each of the protein solutions after the above purification process. Based on the results of the tricine-SDS electrophoretic analysis, the purities were assumed to be as high as not lower than 90%.

The primary sequences of the proteins produced in Examples were the sequences of the C-G29Xs and B-G29Xs with Gly-Pro-Leu-Gly-Ser (derived from the vector pGEX-6P-1) at the N terminal and a Cys residue at the C terminal.

The protein purification by chromatography using the column was performed using an AKTAprime plus system (GE health care, Japan).

Example 7

Analysis of Affinity of Obtained C-G29Xs/B-G29Xs for Immunoglobulin

The obtained C-G29Xs and B-G29Xs were analyzed for the affinity for an immunoglobulin by the biosensor Biacore 3000 (GE health care, Japan) using surface plasmon resonance. In the present example, a human immunoglobulin G drug (hereinafter, referred to as a human IgG) separated from human plasma was used. The human IgG was immobilized on a sensor chip, each of the C-G29Xs and B-G29Xs was added on the chip, and the interaction between them was detected. The human IgG was immobilized on the sensor chip CM5 by amine coupling using N-hydroxysuccinimide (NHS) and N-ethyl-N'-(3-dimethylaminopropyl)carbodiimide hydrochloride (EDC), and ethanolamine was used for blocking (all the sensor chips and the immobilization reagents were available from GE health care, Japan). The human IgG solution was prepared by dissolving Gammagard (Baxter) in a standard buffer (20 mM $NaH_2PO_4$—$Na_2HPO_4$, 150 mM NaCl, pH 7.4) to a concentration of 1.0 mg/mL. The human IgG solution was diluted to 1/100 in an immobilization buffer (10 mM $CH_3COOH$—$CH_3COONa$, pH 4.5) and the human IgG was immobilized on the sensor chip in accordance with the protocol attached to the Biacore 3000. A reference cell to be used as a negative control was also prepared by immobilizing ethanolamine for another flow cell on the chip after activation by EDC/NHS. The C-G29Xs and B-G29Xs were appropriately prepared at concentrations of 10 to 1000 nM using a running buffer (20 mM$NaH_2PO_4$—$Na_2HPO_4$, 150 mM NaCl, 0.005% P-20, pH 7.4) (solutions of three different protein concentrations were prepared for each protein), and each protein solution was added on the sensor chip at a flow rate of 20 µL/min for 30 minutes. A sensorgram of the binding reaction at 25° C. was sequentially plotted during the addition (binding phase, 30 seconds) and after the addition (dissociation phase, 60 seconds). After each sensorgram determination, the sensor chip was regenerated by adding 50 mM NaOH (for 15 seconds) (this process was performed to remove the added proteins remaining on the sensor chip and it was confirmed that the binding activity of the immobilized human IgG was substantially completely recovered). The binding rate constant (kon), dissociation rate constant (koff), affinity constant (KA=kon/koff), and dissociation constant (KD=koff/kon) were calculated by performing a fitting analysis on each of the obtained binding reaction sensorgrams (the binding reaction sensorgrams obtained by subtracting the binding reaction sensorgram of the reference cell) by using the 1:1 binding model in a software BIA evaluation attached to the system. As shown in Table 2, the binding parameters of the C-G29Xs to the human IgG were at similar levels to that of the C-wild (Comparative Example 1). Specifically, the dissociation constants of all the C-G29Xs from the human IgG were in the order of $10^{-8}$ M. Similar results were obtained in the analysis of the B-G29Xs.

TABLE 2

|  | $k_{on}$ (×$10^4$ $M^{-1}$s) | $k_{off}$ ($10^{-3}$ $s^{-1}$) | $K_A$ (×$10^7 M^{-1}$) | $K_D$ (×$10^{-8}$M) |
|---|---|---|---|---|
| B-wild | 8.1 | 4.5 | 1.8 | 5.5 |
| B-G29A | 9.6 | 4.7 | 2 | 4.9 |
| B-G29V | 9.4 | 5.6 | 1.7 | 5.9 |
| B-G29R | 9.5 | 5.3 | 1.8 | 5.6 |
| B-G29D | 7.7 | 5.1 | 1.5 | 6.6 |
| B-G29M | 8.9 | 5.6 | 1.6 | 6.3 |
| B-G29S | 9.4 | 5.2 | 1.8 | 5.6 |
| B-G29W | 11.6 | 5.4 | 2.2 | 4.6 |
| C-wild | 14.5 | 2.1 | 7 | 1.4 |
| C-G29A | 11.3 | 3 | 3.8 | 2.6 |
| C-G29V | 11.9 | 3.6 | 3.3 | 3.1 |
| C-G29R | 11.9 | 3.5 | 3.4 | 2.9 |
| C-G29D | 10 | 3.1 | 3.2 | 3.1 |
| C-G29M | 14.1 | 2.5 | 5.5 | 1.8 |
| C-G29S | 13.7 | 3.4 | 4.1 | 2.5 |
| C-G29L | 13.1 | 3.7 | 3.5 | 2.8 |
| C-G29I | 11.5 | 3.3 | 3.5 | 2.9 |
| C-G29H | 12.5 | 3.8 | 3.3 | 3.1 |
| C-G29F | 13.4 | 2.8 | 4.9 | 2.1 |
| C-G29E | 12.7 | 3.3 | 3.8 | 2.6 |
| C-G29T | 12.2 | 3 | 4.1 | 2.4 |
| C-G29Y | 16.2 | 3.3 | 5 | 2 |
| C-G29W | 13.7 | 3.6 | 3.9 | 2.6 |

Example 8

Preparation of Fab Fragment Derived from Humanized Monoclonal Antibody

In the present invention, the "affinity for the Fab region" was analyzed using an Fab fragment free from the Fc region of an immunoglobulin.

The Fab fragment was prepared by fragmentizing using papain a humanized monoclonal IgG drug chosen as a starting material into an Fab fragment and Fc fragment, and separating and purifying only the Fab fragment.

Specifically, herceptin (humanized monoclonal IgG drug available from Chugai Pharmaceutical Co., Ltd.) was dissolved in a papain digestion buffer (0.1 M AcOH—AcONa, 2 mM EDTA, 1 mM cysteine, pH 5.5). Papain Agarose from papaya latex (papain immobilized agarose available from SIGMA) was added to the solution and the mixture was incubated for about 8 hours at 37° C. while being mixed with a rotator. The Fab fragment (hereinafter, referred to as monoclonal IgG-Fab) was separated and purified from the reaction solution (containing both the Fab fragment and the Fc fragment) which had been separated from the papain immobilized agarose, by ion exchange chromatography using a Resource S column (GE health care, Japan). More specifically, the reaction solution was diluted to a pH of 4.5 in an ion exchange buffer A (50 mM $CH_3COOH$—$CH_3COONa$, pH 4.5), and then added to the Resource S column equilibrated with the ion exchange buffer A. After washing the column with the ion exchange buffer A, the monoclonal IgG-Fab was eluted in the process of salt gradient elution using the ion exchange buffer A and an ion exchange buffer B (50 mM $CH_3COOH$—$CH_3COONa$, 1 M NaCl, pH 4.5) (the buffer B concentration was linearly increased from 0% to 50% in the process of allowing the buffers in an amount corresponding to the volume of 10 columns to pass through the column), and thus separated.

The separated monoclonal IgG-Fab solution was purified by gel filtration chromatography using the Superdex 75 10/300 GL column (a standard buffer was used for equilibration and separation). In this manner, a monoclonal IgG-Fab solution was obtained.

The protein purification by chromatography was performed using the AKTAprime plus system in the same manner as in Example 6.

Example 9

Analysis of Affinity of Obtained C-G29Xs for monoclonal IgG-Fab

The affinity of the obtained C-domain mutants for the IgG-Fab was also analyzed using the Biacore 3000 in the same manner as in Example 7.

The monoclonal IgG-Fab produced in Example 8 was immobilized on the sensor chip CM5 and each C-G29X was added on the chip to detect the interaction between them. Human serum albumin (Sigma Aldrich) was immobilized for a reference cell. Immobilization of the monoclonal IgG-Fab and the human serum albumin was accomplished in the same manner as in Example 6.

Protein solution of different concentrations (4 μM, 8 μM, 16 μM, 32 μM (32 μM samples of some proteins were not prepared)) were prepared from each of the C-G29Xs to be measured using a running buffer (20 mM $NaH_2PO_4$—$Na_2HPO_4$, 150 mM NaCl, 0.005% P-20, pH 7.4). Each protein solution was added on a sensor chip at a flow rate of 20 μL/min for 30 seconds. A sensorgram of the binding reaction at 25° C. was sequentially plotted during the addition (binding phase, 30 seconds) and after the addition (dissociation phase, 60 seconds). After each sensorgram determination, 10 mM NaOH was added for 30 seconds for regeneration of the sensor chip. The measurement was conducted in two runs and the consistency between the experiments was confirmed using the C-G29A (Comparative Example 1) and C-G29D, which were measured twice. The analysis was conducted in the same manner as in Example 7. It should be noted that Rmax, which is one of binding parameters, was regarded as a constant in the fitting analysis. The Rmax is the signal amount detected when molecules added bind to all of the immobilized molecules, and never largely changes in these experiments in which the same molecules (monoclonal IgG-Fab) were immobilized. Since a fitting is incorrectly made so that the Rmax is regarded as an extremely small value if the binding signal is very small, the Rmax was regarded as a constant in the fitting.

FIG. 2 shows sensorgrams of the binding reactions of the C-G29V and C-G29W with the monoclonal IgG-Fab. From a comparison with the sensorgrams of the binding reactions of the C-wild and C-G29A (at the same concentrations, Comparative Example 1) with the monoclonal IgG-Fab as shown together, it was found that almost no monoclonal IgG-Fab binding signal was detected in the result of the C-G29V, for example, although some monoclonal IgG-Fab binding signal was still detected in the result of the C-G29A.

Each of the binding reaction sensorgrams of FIG. 2 was created by subtracting the binding reaction sensorgram of the reference cell from each of the obtained binding reaction sensorgrams. In order from the bottom of each graph, the three reaction sensorgrams are the reaction sensorgrams at concentrations of the added protein of 4 μM, 8 μM and 16 μM, and all are displayed together. The vertical axis indicates the binding response difference (RU) and the horizontal axis indicates the time (second)

Table 3 shows the affinity constants of the C-domain mutants for the monoclonal IgG-Fab. N.D. means that no binding signal was detected. The mutants C-G29V, C-G29L, C-G29Y, C-G29F, C-G29T, C-G29W, C-G29D, C-G29E, C-G29R, C-G29H and C-G29M had significantly lower affinity constants than C-G29A. Regarding the C-G29I, no binding signal could be detected. This result indicates that the C-G29I was significantly weak in binding to the monoclonal IgG-Fab than C-G29A.

TABLE 3

| First measurement | | Second measurement | |
|---|---|---|---|
| | $K_A (\times 10^4 M^{-1})$ | | $K_A (\times 10^4 M^{-1})$ |
| C-G29A | 8.1 | C-G29A | 7.4 |
| C-G29D | 0.26 | C-G29D | 0.30 |
| C-G29V | 0.16 | C-G29H | 0.16 |
| C-G29L | 0.33 | C-G29F | 0.11 |
| C-G29R | 0.13 | C-G29E | 0.095 |
| | | C-G29T | 0.14 |
| | | C-G29Y | 0.11 |
| | | C-G29W | 0.31 |
| | | C-G29M | 0.40 |
| | | C-G29I | N.D. |

Example 10

Alkali Resistance Evaluation of B-G29Xs

The alkali resistance was evaluated for B-G29Xs by comparing decreases in the binding amount to a human IgG (remaining binding activity to the human IgG) after incubation in an alkaline condition for a predetermined time period.

Specifically, the binding amount to the human IgG was measured for the B-G29Xs using the Biacore 3000 before and after an alkali treatment. In the alkali treatment, 26.2 µM of each B-domain mutant (10 µL) was mixed with a certain amount of 0.625 M NaOH to a final concentration of 0.5 M. The mixture was incubated for 20 hours at 30° C. Subsequently, 0.5 M HCl (in an amount that had been confirmed to neutralize the pH) was added to each treated solution to neutralize the solution. The solution was further diluted in a running buffer (20 mM $NaH_2PO_4$—$Na_2HPO_4$, 150 mM NaCl, 0.005% P-20, pH 7.4) to ½. In this manner, solutions of the B-G29Xs after the alkali treatment were prepared. In order to achieve the same protein concentration and composition of the solutions, solutions of the B-G29Xs before the alkali treatment were prepared by preparing a mixed solution of the NaOH solution for the alkali treatment and the HCl solution for the neutralization treatment in advance, and adding the mixed solution to each of the B-G29Xs (26.2 µM, 10 µL). Preparation of sensor chips (e.g. immobilization of the human IgG), running buffers used for the measurement, the measurement temperature, and the regeneration treatment of the chips were the same as those in Example 7. Each of the solutions of the B-G29Xs before and after the alkali treatment was added on the sensor chip at a flow rate of 20 µL/min for 150 seconds. A binding reaction sensorgram was sequentially plotted during the addition (binding phase, 150 seconds) and after the addition (dissociation phase, 210 seconds). The analysis was conducted in the same manner as in Example 7. Here, the interpretation of the obtained binding parameters will be described. In this analysis, the protein concentrations before and after the alkali treatment were controlled to be the same, but the concentration of a protein having binding activity to a human IgG changes. However, since fitting using the concentration as a variable is difficult, the concentration was considered to be constant before and after the treatment in the fitting analysis. In this case, the concentration change of a protein having binding activity to IgG is reflected on the parameter Rmax, which is the maximum binding capacity. Therefore, the alkali resistance was evaluated by calculating, for each B-G29X, the relative value of the Rmax after the alkali treatment to the Rmax before the alkali treatment (remaining IgG binding activity (%)) for comparison.

Figure 3:
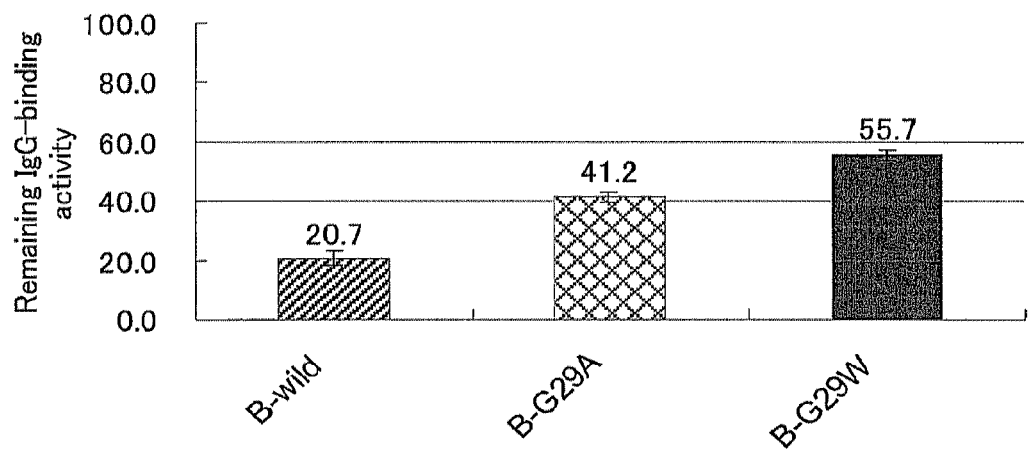
FIG. 3 is a graph of remaining IgG binding activities (%) after an alkali treatment of B-G29Xs, B-wild and B-G29A of Example 10 of the present invention and Comparative Example 1.

As shown in FIG. 3, the remaining IgG binding activity after the alkali treatment of the B-G29A (Comparative Example 1) was 41.2%, and that of the B-G29W was 55.7%, which is significantly higher than that of the B-G29A. Thus, the B-G29W had higher alkali resistance than the B-G29A.

Example 11

Alkali Resistance Evaluation of C-G29Xs

The alkali resistance of C-G29Xs was evaluated in the same manner as in Example 10, except that the incubation time in the alkali treatment was different from that of Example 10 and the incubation was performed at 30° C. for 25 hours.

Figure 4:
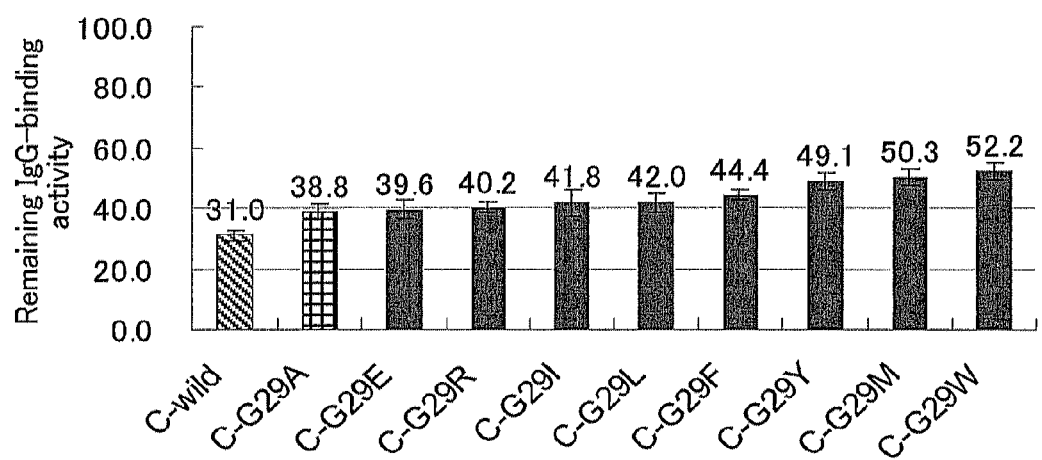
FIG. 4 is a graph of remaining IgG binding activities (%) after an alkali treatment of C-G29Xs, C-wild and C-G29A of Example 11 of the present invention and Comparative Example 1.

As shown in FIG. 4, the remaining IgG binding activities after the alkali treatment of the C-G29R, C-G29M, C-G29L, C-G29I, C-G29F, C-G29E, C-G29Y, and C-G29W were higher than that of the C-G29A (Comparative Example 1). In particular, the C-G29M, C-G29F, C-G29Y, and C-G29W had higher remaining IgG binding activities and were shown to have higher alkali resistance than that of the C-G29A.

Example 12

Preparation of DNA Encoding Five Connected C-G29Vs

A base sequence encoding a protein consisting of five-connected C-G29Vs was constructed by reverse translation from the amino acid sequence (SEQ ID NO:57) of the protein. The codons were distributed so that the codon usage frequency of the protein was closer to the codon usage frequency of the cell surface protein HWP, which is expressed in a large amount in *Brevibacillus choshinensis* HPD31 (Ebisu S., "J. Bacteriol.", 1990, No. 172, pages 1312-1320), and that the sequence identities of the base sequences of the five domains were low. The restriction enzyme recognition sites PstI and XbaI were produced on the 5' side and 3' side, respectively, of the sequence encoding the five-connected domains. The DNA fragment was produced by Takara Bio, Inc. The sequence of the produced DNA fragment is shown as SEQ ID NO:58.

FIG. 5 shows the base sequences of the five domains for comparison, and Table 4 shows the percentages of the sequence identities between the base sequences of the domains (the domains are numbered from 1 to 5 in the order from the N terminal). Table 4 shows the percentages of matched bases based on the length of 174 bp encoding a single domain unit. As a result of the codon distribution, even the highest sequence identity of the combination of the base sequences (domains 2 and 5) was suppressed to not higher than 85%.

The produced DNA fragment encoding the five connected C-G29Vs was digested with PstI and XbaI (both available from Takara), and then separated and purified by agarose gel electrophoresis. Separately, the plasmid vector pNK3262 for *Brevibacillus* was digested with PstI and XbaI, and purified and recovered. The recovered vector was treated with alkaline phosphatase for dephosphorylation (Takara). Both were mixed and ligated with Ligation High (TOYOBO CO., LTD.). In this manner, a plasmid vector pNK3262-C-G29V capable of expressing five connected C-G29Vs was constructed. *Brevibacillus choshinensis* FY-1 was transformed using the plasmid vector obtained by the above procedure. The transformation was accomplished by a known electroporation ("Biosci. Biotech. Biochem.", 1997, No. 61, pages 202-203). *Brevibacillus choshinensis* FY-1 is a Phe and Tyr requiring strain obtained by mutating *Brevibacillus choshinensis* HPD31-OK (JP H6-296485 A).

TABLE 4

| Query | Target | Match | % |
|---|---|---|---|
| Domain 1 | Domain 2 | 136 bp | 78.2 |
| Domain 1 | Domain 3 | 143 bp | 82.2 |
| Domain 1 | Domain 4 | 141 bp | 81.0 |
| Domain 1 | Domain 5 | 140 bp | 80.5 |
| Domain 2 | Domain 3 | 135 bp | 77.6 |
| Domain 2 | Domain 4 | 137 bp | 78.7 |
| Domain 2 | Domain 5 | 147 bp | 84.5 |
| Domain 3 | Domain 4 | 132 bp | 75.9 |
| Domain 3 | Domain 5 | 144 bp | 82.8 |
| Domain 4 | Domain 5 | 129 bp | 74.1 |

Example 13

Expression of Target Protein in Recombinant Bacterium Capable of Expressing Five Connected C-G29Vs and Analysis of Plasmid Vector Contained Therein The *Brevibacillus choshinensis* FY-1 recombinant bacterium obtained in Example 12 was cultured with shaking for 3 days at 30° C. in 5 mL of 3YC medium (polypeptone 3%, yeast extract 0.2%, glucose 3%, magnesium sulfate 0.01%, iron sulfate 0.001%, manganese chloride 0.001%, zinc chloride 0.0001%) containing 60 μg/mL neomycin.

After the culture, the cells were separated by centrifugation and a 5 μL aliquot of the supernatant was analyzed by SDS-PAGE by a common technique. As a result, as shown in FIG. 6A, a band at a molecular weight of about 33,000, which was assumed to be the five connected C-G29Vs, was detected. Unlike the same SDS-PAGE analysis on the culture supernatant of the recombinant bacterium capable of expressing the five connected C-wilds (Comparative Example 2, FIG. 6B), no band that suggests a protein in which the number of the domains is reduced was detected.

A plasmid was obtained by a common technique from the cells after shake culturing, and digested with PstI and XbaI. The agarose gel electrophoretic analysis on the resulting fragments revealed the presence of a fragment (about 890 bp) corresponding to a DNA fragment encoding the five connected C-G29Vs, as shown in FIG. 7A. Unlike the same analysis of a plasmid vector contained in the five connected C-wild expression recombinant bacterium (Comparative Example 2, FIG. 7B), no DNA frayment corresponding to one encoding a reduced number of domains was detected.

Although the DNA fragments each encoding one of the five connected domains have the base sequence 100% the same in Example 2, the base sequence identities between the domains in the present example were reduced to not higher than 85% as a result of changes of the codons. Therefore, homologous recombination within the molecule was remarkably inhibited and no partial deletion occurred in the DNA fragment. As a result, the plasmid was stabilized. In the present example, the DNA encoding the five connected C-wilds (Comparative Example 2) was a comparison target, but it should be noted that the present example is not intended for a comparison between the amino acid sequences of the C-wild and C-G29V but is intended for a comparison between the case where the sequence identities between the base sequences each encoding one of domains are 100% the same and the case where the sequence identities are reduced to not higher than 85%.

Example 14

Production of Five Connected C-G29Ws and Five Connected C-G29Ys

The gene encoding five connected C-G29Vs in the plasmid pNK3262-C-G29V produced in Example 13 was cleaved into five DNA fragments so that each fragment included the codon of Val-29 of one of the domains. The DNA for the domain 1 was digested with PstI and NarI; the DNA for the domain 2 was digested with NarI and HindIII; the DNA for the domain 3 was digested with HindIII and MluI; the DNA for the domain 4 was digested with MluI and BglII; and the DNA for the domain 5 was digested with BglII and XbaI (NarI was available from TOYOBO Co., Ltd. and others were available from Takara). The respective resulting DNA fragments (SEQ ID NOs:59 to 63) were recovered by separation and purification using an agarose gel.

The cloning vector pSL301 (Invitrogen) was digested using the same pair of restriction enzymes as those used for each of the DNA fragments encoding the domains. The resulting fragment was mixed with the DNA fragment and they were ligated with Ligation High. In this manner, plasmids each containing one of the five DNA fragments into which the gene was cleaved were constructed. The plasmids are represented in correspondence to the numbers of the domains as pSL301-V29-d1, pSL301-V29-d2, pSL301-V29-d3, pSL301-V29-d4 and pSL301-V29-d5.

The quick change technique was performed using the oligonucleotide primers of SEQ ID NOs:64 to 73, and the plasmids pSL301-V29-d1, pSL301-V29-d2, pSL301-V29-d3, pSL301-V29-d4 and pSL301-V29-d5 as templates. As a result, plasmids pSL301-W29-d1, pSL301-W29-d2, pSL301-W29-d3, pSL301-W29-d4 and pSL301-W29-d5 each containing a DNA fragment encoding a domain in which the Val-29 of one of the domains was replaced with Trp (SEQ ID NOs:74 to 78) were formed. After confirming the introduced mutations, the five fragments were sequentially ligated to one another with Ligation High. In this manner, a DNA fragment encoding five connected C-G29Ws (SEQ ID NO:79) was constructed.

Plasmids pSL301-Y29-d1, pSL301-Y29-d2, pSL301-Y29-d3, pSL301-Y29-d4, and pSL301-Y29-d5 each containing a DNA fragment in which the Val-29 was replaced with Tyr (SEQ ID NOs:90 to 94) were constructed using the oligonucleotide primers of SEQ ID NOs:80 to 89 in the same manner as described above. After confirming the introduced mutations, the five fragments were ligated to one another with Ligation High. In this manner, a DNA fragment encoding five connected C-G29Ys (SEQ ID NO:95) was constructed.

The DNA fragment encoding five connected C-G29Ws (SEQ ID NO:79) and the DNA fragment encoding five connected C-G29Ys (SEQ ID NO:95) produced by the above procedure were digested with PstI and XbaI, and then separated and purified by agarose gel electrophoresis. Separately, the plasmid vector pNK3262 for *Brevibacillus* was digested with PstI and XbaI, and then purified and recovered. The recovered vector was treated with alkaline phosphatase for dephosphorylation. Both were mixed and ligated with Ligation High. In this manner, a plasmid pNK3262-C-G29W capable of expressing the five connected C-G29Ws and a plasmid pNK3262-C-G29Y capable of expressing the five connected C-G29Ys were obtained. *Brevibacillus choshinensis* FY-1 cells were transformed using these plasmids.

The recombinant *Brevibacillus choshinensis* FY-1 cells obtained by the above operation were cultured with shaking in 5 mL of 3YC medium containing 60 μg/mL neomycin for three days at 30° C. After the culture, the cells were separated by centrifugation and a 5 μL aliquot of the supernatant of each transformant culture was analyzed by SDS-PAGE by a common technique. As a result, bands assumed to be the five connected C-G29Ws and the five connected C-G29Ys were detected at positions corresponding to a molecular weight of about 33,000.

Comparative Example 1

Experiment of Wild-type and G29A Mutant

From transformants containing the C-wild expression plasmid obtained in Example 1 and the B-wild expression plasmid obtained in Example 2, purified protein solutions of the C-wild and B-wild were obtained in the same manner as in Examples 5 and 6. Transformants containing a C-G29A expression plasmid and a B-G29A expression plasmid were obtained using the primers of SEQ ID NOs:96 and 97 by the same technique as in Example 3. The protein sequence of the C-G29A is shown as SEQ ID NO:98, and the protein sequence of the B-G29A is shown as SEQ ID NO:99. The base sequences of coding DNAs were determined in the same manner as in Example 3, and purified protein solutions of the C-G29A and B-G29A were obtained in the same manner as in Examples 5 and 6. As control experiments, the same experiments as those performed on the C-G29Xs in Examples 7, 9 and 11 were also performed on the C-wild and C-G29A. As control experiments, the B-wild and B-G29A were subjected to the same experiments as those performed on the B-G29Xs in Examples 7 and 10.

Comparative Example 2

Experiment of Five Connected C-wilds

A first half part of the C-wild was amplified by PCR using the oligonucleotide primers of SEQ ID NOs:100 and 101, and the expression vector pNK3262NX encoding wild-type Protein A as a template. The remaining second half of the C-wild was amplified by PCR using the oligonucleotide primers of SEQ ID NOs:102 and 103. After purifying both the PCR fragments, the fragments were mixed and overlapped with each other at the site at which the oligonucleotide primers of SEQ ID NOs:100 and 103 can be annealed. Using this as a template and the oligonucleotide primers of SEQ ID NOs:101 and 102, the second PCR was performed. As a result of this procedure, the first half and the second half of the C-wild were replaced with each other, and the resulting DNA fragment had HindIII recognition sites on both ends (SEQ ID NO:104). The obtained DNA fragment was digested with HindIII (Takara), and then purified and recovered.

The *Escherichia coli* cloning vector pBluescriptII KS (−) (Stratagene) was digested with HindIII, and then purified and recovered. The recovered vector was treated with alkaline phosphatase (Takara) for dephosphorylation. The DNA fragment of SEQ ID NO: 104 digested with HindIII was ligated thereto with the DNA ligase Ligation High (TOYOBO Co., Ltd.). In this manner, a plasmid was constructed. *Escherichia coli* HB 101 (Takara) was transformed using the obtained plasmid, and the plasmid DNA was amplified and extracted by a common technique. The plasmid DNA was partially digested with HindIII and the DNA fragment cleaved at one site was separated and purified by an agarose gel and then treated with alkaline phosphatase for dephosphorylation. The DNA fragment of SEQ ID NO:104 digested with HindIII was ligated to the plasmid with Ligation High. *Escherichia coli* HB 101 was transformed in the same manner and the plasmid DNA was prepared. Then, a plasmid DNA in which two DNA fragments of SEQ ID NO:104 were ligated in tandem at the HindIII site was recovered.

PCR was performed using the oligonucleotide primers of SEQ ID NOs: 105 and 106 and the plasmid DNA obtained by the above procedure as a template. The oligonucleotide primers of SEQ ID NOs:105 and 106 were designed such that Met-Ala-Phe-Ala was added on the N-terminal side (upstream of Ala-1) of the C-wild domain, that a stop codon was located on the C-terminal side (downstream of Lys-58), and that the DNA sequence encoding the domain had XhoI and NcoI restriction enzyme recognition sites on the 5' side and a BamHI restriction enzyme recognition site on the 3' side. By the above procedure, the DNA fragment encoding the C-wild domain and having the XhoI and NcoI restriction enzyme recognition sites on the 5' side, the HindIII restriction enzyme recognition site around the center of the fragment, and the BamHI restriction enzyme recognition site on the 3' side was amplified. The obtained DNA sequence is shown as SEQ ID NO: 107. The DNA fragment of SEQ ID NO:107 was digested with XhoI and BamHI (both available from Takara), and then purified and recovered.

The *Escherichia coli* cloning vector pBluescriptII KS (−) was digested with XhoI and BamHI, and then purified and recovered. The recovered vector was treated with alkaline phosphatase for dephosphorylation. The DNA fragment of SEQ ID NO:107 and the pBluescriptII KS (−) were ligated with Ligation High. *Escherichia coli* HB101 was transformed using this and the plasmid DNA was amplified and extracted by a common technique.

The plasmid containing the DNA fragment encoding the C-wild produced by the above procedure was digested with HindIII, and then purified and recovered. The recovered plasmid was treated with alkaline phosphatase for dephosphorylation. This plasmid and the DNA fragment of SEQ ID NO:104 were ligated with Ligation High. In this manner, a plasmid having a DNA fragment encoding two C-wilds connected in tandem was constructed. *Escherichia coli* HB101 was transformed using the obtained plasmid and the plasmid DNA was amplified and extracted by a common technique. The extracted plasmid was partially digested with HindIII and the DNA fragment cleaved at one site was separated and purified by an agarose gel and then treated with alkaline phosphatase for dephosphorylation. This plasmid was ligated to the DNA fragment of SEQ ID NO:104 with Ligation High. In this manner, a plasmid having a DNA fragment encoding three C-wilds connected in tandem was constructed. Likewise, a plasmid having a DNA fragment encoding five C-wilds connected in tandem was constructed and *Escherichia coli* HB101 was transformed in the same manner. The plasmid DNA was amplified and extracted by a common technique. The plasmid was digested with NcoI and BamHI (both available from Takara), separated using an agarose gel, and then purified and recovered. In this manner, a DNA fragment encoding five connected C-wilds was prepared.

The plasmid vector pNK3262 for *Brevibacillus* was digested with NcoI and BamHI, and then purified and recovered. The recovered vector was treated with alkaline phosphatase for dephosphorylation. The DNA fragment encoding five connected C-wilds prepared by the above procedure was ligated thereto with Ligation High. In this manner, a plasmid vector pNK3262-C-wild capable of expressing the five connected C-wilds was constructed. *Brevibacillus choshinensis* FY-1 was transformed using the plasmid vector obtained by this procedure.

The recombinant *Brevibacillus choshinensis* FY-1 cells obtained by the above procedure were cultured with shaking in 5 mL of 3YC medium containing 60 µg/mL neomycin for three days at 30° C. After the culture, the cells were separated by centrifugation and a 5 µL aliquot of the supernatant was analyzed by SDS-PAGE by a common technique. As shown in FIG. 6B, bands suggesting the presence of proteins whose connected domains reduced to 4, 3 or 2 domains were detected in addition to a band assumed to be the pentamer of the five connected C-wilds at a position corresponding to a molecular weight of about 33,000.

A plasmid was obtained by a common technique from the cells obtained by the shake culturing, and digested with NcoI and BamHI, and then analyzed by agarose gel electrophoresis. As shown in FIG. 7B, bands suggesting the presence of DNA fragments corresponding to those encoding 4, 3 or 2 connected domains were detected in addition to a band indicating an about 890 bp fragment corresponding to the DNA fragment encoding the five connected C-wilds. The electrophoretic pattern was well in accord with the pattern of the bands of the protein obtained by SDS-PAGE. The sequence analysis of these DNA fragments revealed partial gene deletions of domain size. This may be explained as follows. Because the sequences of the DNA fragments encoding each domain of the five connected C-wilds are 100% the same, homologous recombination in the plasmid molecule is likely to occur, resulting in plasmid vectors for a reduced number of domains. As a result, proteins translated from these vectors are assumed to coexist.

The invention claimed is:

1. A protein having an affinity for an immunoglobulin, comprising an amino acid sequence derived from,
   C domain of protein A of SEQ ID NO: 5,
wherein a glycine (Gly) residue corresponding to position 29 of the C domain, which is conserved in the C domain of Protein A, is replaced with an amino acid other than alanine (Ala), and
   the protein has a lower affinity for a Fab region of an immunoglobulin than a protein comprising an amino acid sequence in which the Gly residue is replaced with Ala,
wherein the amino acid other than Ala is any of leucine (Leu), isoleucine (Ile), phenylalanine (Phe), tyrosine (Tyr), tryptophan (Trp), glutamic acid (Glu), arginine (Arg), and methionine (Met), and which has 85% or higher sequence identity to the amino acid sequence of SEQ ID NO: 5.

2. The protein according to claim 1,
wherein the Gly residues corresponding to position 29 of the C domain is the Gly residue at position 29 of the C domain.

3. The protein according to claim 1,
wherein the amino acid sequence before introduction of the mutation is an amino acid sequence of SEQ ID NO: 5.

4. The protein according to claim 1,
which has improved chemical stability in an alkaline condition compared to a protein having an amino acid sequence before introduction of the mutation.

5. The protein according to claim 1,
wherein the amino acid sequence after introduction of the mutation is any of amino acid sequences of SEQ ID NOs: 6 to 18.

6. A multi-domain protein,
wherein two or more of the proteins according to claim 1 are connected together.

7. A multi-domain protein,
wherein two or more different proteins selected from the proteins according to claim 1 are connected together.

8. The multi-domain protein according to claim 6,
wherein the number of the domains is 2 to 5.

9. An affinity separation matrix, comprising the protein according to claim 1 as affinity ligand,
wherein the protein is immobilized on a carrier made of a water-insoluble base material.

10. The affinity separation matrix according to claim 9, which binds to a protein containing an Fc region of an immunoglobulin.

11. The affinity separation matrix according to claim 10,
wherein the protein containing an Fc region of an immunoglobulin is an antibody, antibody derivative, antibody fragment, or antibody fragment derivative.

12. The affinity separation matrix according to claim 11,
wherein the antibody, antibody derivative, antibody fragment, or antibody fragment derivative is an IgG or an IgG derivative.

13. An affinity separation matrix, comprising the multi-domain protein according to claim 6 as an affinity ligand,
wherein the protein is immobilized on a carrier made of a water-insoluble base material.

14. A DNA encoding the protein according claim 1.

15. A DNA encoding the multi-domain protein according to claim 6.

16. A vector comprising the DNA according to claim 14.

17. A transformant which is obtainable by transformation of a host with the vector according to claim 16.

18. The transformant according to claim 17,
wherein the host is a gram-positive bacterium.

19. The transformant according to claim 18,
wherein the gram-positive bacterium is a bacterium of *Brevibacillus*.

20. The transformant according to claim 19,
wherein the bacterium of *Brevibacillus* is *Brevibacillus choshinensis*.

21. The DNA according to claim 15,
wherein nucleotide sequences encoding the domains have 90 % or lower sequence identity to one another.

22. A method for producing the protein according to claim 1, the method comprising:

utilizing the transformant which is obtainable by transformation of a host with a vector comprising DNA encoding the protein according to claim 1.

23. The production method according to claim 22, further comprising:

accumulating the protein intracellularly or in a periplasmic space of the transformant; and/or extracellularly secreting the protein from the transformant.

24. A method for separating a protein containing an Fc region of an immunoglobulin, comprising adsorbing the protein containing the Fc region of the immunoglobulin on the affinity separation matrix according to claim 9.

25. A method for producing the protein according claim 1, the method comprising:

utilizing a cell-free protein synthesis system using a DNA encoding the protein according to claim 1.

26. A method for producing the multi-domain protein according to claim 6, the method comprising:

utilizing a transformant which is obtainable by transformation of a host with a vector comprising DNA encoding the multi-domain protein according to claim 6.

27. A method for producing the multi-domain protein according to claim 6, the method comprising:

utilizing a cell-free protein synthesis system using a DNA encoding the protein according to claim 6.

* * * * *